(12) United States Patent
Bonsignore et al.

(10) Patent No.: US 10,092,427 B2
(45) Date of Patent: Oct. 9, 2018

(54) ALTERNATING CIRCUMFERENTIAL BRIDGE STENT DESIGN AND METHODS FOR USE THEREOF

(75) Inventors: Craig Bonsignore, Pleasanton, CA (US); Stephen J. Kleshinski, San Jose, CA (US)

(73) Assignee: Confluent Medical Technologies, Inc., Fremont, CA (US)

( * ) Notice: Subject to any disclaimer, the term of this patent is extended or adjusted under 35 U.S.C. 154(b) by 794 days.

(21) Appl. No.: 12/939,894

(22) Filed: Nov. 4, 2010

(65) Prior Publication Data
US 2011/0106237 A1    May 5, 2011

Related U.S. Application Data

(60) Provisional application No. 61/391,462, filed on Oct. 8, 2010, provisional application No. 61/290,836, filed
(Continued)

(51) Int. Cl.
| | | |
|---|---|---|
| *A61F 2/915* | (2013.01) | |
| *A61F 2/04* | (2013.01) | |
| *A61M 1/36* | (2006.01) | |

(52) U.S. Cl.
CPC ........ *A61F 2/915* (2013.01); *A61F 2002/046* (2013.01); *A61F 2002/91541* (2013.01);
(Continued)

(58) Field of Classification Search
CPC ...... A61F 2002/91558; A61F 2002/915; A61F 2250/0012; A61F 2250/0018
(Continued)

(56) References Cited

U.S. PATENT DOCUMENTS

| | | | |
|---|---|---|---|
| 3,593,854 | A | 7/1971 | Swank |
| 3,659,593 | A | 5/1972 | Vail |
| | | (Continued) | |

FOREIGN PATENT DOCUMENTS

| | | |
|---|---|---|
| EP | 0362113 A1 | 4/1990 |
| EP | 0221570 B1 | 1/1991 |
| | (Continued) | |

OTHER PUBLICATIONS

Duerig et al.; An overview of superelastic stent design; Min Invas Ther & Allied Technol; vol. 9(3/4); pp. 235-246; 2000.
(Continued)

*Primary Examiner* — Brian Pellegrino
(74) *Attorney, Agent, or Firm* — Shay Glenn LLP

(57) ABSTRACT

A stent includes a first section and a second section. The first section and the second section each include a plurality of expandable modules and a plurality of bridging modules. Each expandable module includes a plurality of strut elements that join together at a plurality of apices, and each bridging module includes bridging elements that connect an apex of a first module with an apex of a second module. In some aspects, the first section is more flexible along the longitudinal axis of the stent than the second section and is configured to be placed in a specific region of a vessel that requires flexibility to accommodate surrounding anatomy. In some aspects, the first section is more radially stiff than the second section and is configured to be placed in a specific region of the vessel that requires radial stiffness to counteract crushing force caused by surrounding anatomy.

10 Claims, 16 Drawing Sheets

Related U.S. Application Data on Dec. 29, 2009, provisional application No. 61/258,145, filed on Nov. 4, 2009.

(52) U.S. Cl.
CPC ............... *A61F 2002/91575* (2013.01); *A61F 2230/0054* (2013.01); *A61F 2250/0018* (2013.01); *A61F 2250/0019* (2013.01); *A61F 2250/0036* (2013.01); *A61M 1/3655* (2013.01)

(58) Field of Classification Search
USPC .............................. 623/1.15, 1.3, 1.31, 1.22
See application file for complete search history.

(56) References Cited

U.S. PATENT DOCUMENTS

| | | |
|---|---|---|
| 3,765,536 A | 10/1973 | Rosenberg |
| 3,765,537 A | 10/1973 | Rosenberg |
| 3,788,328 A | 1/1974 | Alley et al. |
| 3,807,401 A | 4/1974 | Riggle et al. |
| 3,843,974 A | 10/1974 | Miller et al. |
| 3,874,388 A | 4/1975 | King et al. |
| 3,935,111 A | 1/1976 | Bentley |
| 3,952,747 A | 4/1976 | Kimmell, Jr. |
| 3,953,566 A | 4/1976 | Gore |
| 3,970,565 A | 7/1976 | Ahlstrand et al. |
| 4,007,743 A | 2/1977 | Blake |
| 4,014,318 A | 3/1977 | Dockum et al. |
| 4,016,884 A | 4/1977 | Kwan-Gett |
| 4,073,723 A | 2/1978 | Swank et al. |
| 4,101,984 A | 7/1978 | MacGregor |
| 4,115,277 A | 9/1978 | Swank |
| 4,157,965 A | 6/1979 | Raible |
| 4,303,530 A | 12/1981 | Shah et al. |
| 4,319,580 A | 3/1982 | Colley et al. |
| 4,353,996 A | 10/1982 | Marconi et al. |
| 4,374,669 A | 2/1983 | MacGregor |
| 4,425,908 A | 1/1984 | Simon |
| 4,444,198 A | 4/1984 | Petre |
| 4,447,227 A | 5/1984 | Kotsanis |
| 4,457,487 A | 7/1984 | Steigerwald |
| 4,494,531 A | 1/1985 | Gianturco |
| 4,523,592 A | 6/1985 | Daniel |
| 4,542,748 A | 9/1985 | Roy |
| 4,553,545 A | 11/1985 | Maass et al. |
| 4,565,823 A | 1/1986 | Ohata et al. |
| 4,586,501 A | 5/1986 | Claracq |
| 4,592,356 A | 6/1986 | Gutierrez |
| 4,616,656 A | 10/1986 | Nicholson et al. |
| 4,619,246 A | 10/1986 | Molgaard-Nielsen et al. |
| 4,627,836 A | 12/1986 | MacGregor |
| 4,642,089 A | 2/1987 | Zupkas et al. |
| 4,643,184 A | 2/1987 | Mobin-Uddin |
| 4,650,466 A | 3/1987 | Luther |
| 4,655,771 A | 4/1987 | Wallsten |
| 4,662,885 A | 5/1987 | DiPisa, Jr. |
| 4,664,682 A | 5/1987 | Monzen |
| 4,666,426 A | 5/1987 | Aigner |
| 4,666,543 A | 5/1987 | Kawano |
| 4,676,771 A | 6/1987 | Henke |
| 4,680,029 A | 7/1987 | Ranford et al. |
| 4,688,553 A | 8/1987 | Metals |
| 4,699,611 A | 10/1987 | Bowden |
| 4,722,724 A | 2/1988 | Schocket |
| 4,727,873 A | 3/1988 | Mobin-Uddin |
| 4,732,152 A | 3/1988 | Wallsten |
| 4,756,884 A | 7/1988 | Hillman et al. |
| 4,760,849 A | 8/1988 | Kropf |
| 4,774,949 A | 10/1988 | Fogarty |
| 4,781,177 A | 11/1988 | Lebigot |
| 4,790,329 A | 12/1988 | Simon |
| 4,793,348 A | 12/1988 | Palmaz |
| 4,795,446 A | 1/1989 | Fecht |
| 4,817,600 A | 4/1989 | Herms et al. |
| 4,826,478 A | 5/1989 | Schocket |
| 4,828,563 A | 5/1989 | Muller-Lierheim |
| 4,832,055 A | 5/1989 | Palestrant |
| 4,858,623 A | 8/1989 | Bradshaw et al. |
| 4,873,978 A | 10/1989 | Ginsburg |
| 4,899,543 A | 2/1990 | Romanelli et al. |
| 4,917,089 A | 4/1990 | Sideris |
| 4,923,464 A | 5/1990 | DiPisa, Jr. |
| 4,944,727 A | 7/1990 | McCoy |
| 4,946,457 A | 8/1990 | Elliott |
| 4,954,251 A | 9/1990 | Barnes et al. |
| 4,957,501 A | 9/1990 | Lahille et al. |
| 4,969,891 A | 11/1990 | Gewertz |
| 4,969,902 A | 11/1990 | Ravo |
| 4,986,279 A | 1/1991 | O'Neill |
| 4,990,156 A | 2/1991 | Lefebvre |
| 5,018,530 A | 5/1991 | Rank et al. |
| 5,059,205 A | 10/1991 | El-Nounou et al. |
| 5,071,407 A | 12/1991 | Termin et al. |
| 5,092,996 A | 3/1992 | Spielberg |
| 5,102,417 A | 4/1992 | Palmaz |
| 5,108,407 A | 4/1992 | Geremia et al. |
| 5,108,418 A | 4/1992 | Lefebvre |
| 5,108,419 A | 4/1992 | Reger et al. |
| 5,108,420 A | 4/1992 | Marks |
| 5,127,916 A | 7/1992 | Spencer et al. |
| 5,133,733 A | 7/1992 | Rasmussen et al. |
| 5,147,379 A | 9/1992 | Sabbaghian et al. |
| 5,151,105 A | 9/1992 | Kwan-Gett |
| 5,152,777 A | 10/1992 | Goldberg et al. |
| 5,158,533 A | 10/1992 | Strauss et al. |
| 5,158,565 A | 10/1992 | Marcadis et al. |
| 5,171,259 A | 12/1992 | Inoue |
| 5,190,657 A | 3/1993 | Heagle et al. |
| 5,192,286 A | 3/1993 | Phan et al. |
| 5,192,301 A | 3/1993 | Kamiya et al. |
| 5,195,984 A | 3/1993 | Schatz |
| 5,197,978 A | 3/1993 | Hess |
| 5,201,757 A | 4/1993 | Heyn et al. |
| 5,234,458 A | 8/1993 | Metais |
| 5,257,621 A | 11/1993 | Bardy et al. |
| 5,269,924 A | 12/1993 | Rochat |
| 5,273,517 A | 12/1993 | Barone et al. |
| 5,275,622 A | 1/1994 | Lazarus et al. |
| 5,282,823 A | 2/1994 | Schwartz et al. |
| 5,284,488 A | 2/1994 | Sideris |
| 5,292,321 A | 3/1994 | Lee |
| 5,300,086 A | 4/1994 | Gory et al. |
| 5,311,908 A | 5/1994 | Barone et al. |
| 5,334,217 A | 8/1994 | Das |
| 5,344,427 A | 9/1994 | Cottenceau et al. |
| 5,350,398 A | 9/1994 | Pavcnik et al. |
| 5,354,317 A | 10/1994 | Alt |
| 5,356,432 A | 10/1994 | Rutkow et al. |
| 5,366,504 A | 11/1994 | Andersen et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,421,832 A | 6/1995 | Lefebvre |
| 5,423,851 A | 6/1995 | Samuels |
| 5,425,744 A | 6/1995 | Fagan et al. |
| 5,433,727 A | 7/1995 | Sideris |
| 5,443,500 A | 8/1995 | Sigwart |
| 5,449,373 A | 9/1995 | Pinchasik et al. |
| 5,449,382 A | 9/1995 | Dayton |
| 5,451,233 A | 9/1995 | Yock |
| 5,451,235 A | 9/1995 | Lock et al. |
| 5,464,449 A | 11/1995 | Ryan et al. |
| 5,466,216 A | 11/1995 | Brown et al. |
| 5,480,423 A | 1/1996 | Ravenscroft et al. |
| 5,484,424 A | 1/1996 | Cottenceau et al. |
| 5,486,193 A | 1/1996 | Bourne et al. |
| 5,503,801 A | 4/1996 | Brugger |
| 5,507,811 A | 4/1996 | Koike et al. |
| 5,522,881 A | 6/1996 | Lentz |
| 5,527,338 A | 6/1996 | Purdy |
| 5,531,788 A | 7/1996 | Dibie et al. |
| 5,545,206 A | 8/1996 | Carson |

(56) References Cited

U.S. PATENT DOCUMENTS

| | | |
|---|---|---|
| 5,545,210 A | 8/1996 | Hess et al. |
| 5,549,626 A | 8/1996 | Miller et al. |
| 5,554,182 A | 9/1996 | Dinh et al. |
| 5,562,698 A | 10/1996 | Parker |
| 5,569,273 A | 10/1996 | Titone et al. |
| 5,571,166 A | 11/1996 | Dinh et al. |
| 5,578,045 A | 11/1996 | Das |
| 5,591,197 A | 1/1997 | Orth et al. |
| 5,591,224 A | 1/1997 | Schwartz et al. |
| 5,591,227 A | 1/1997 | Dinh et al. |
| 5,591,251 A | 1/1997 | Brugger |
| 5,593,441 A | 1/1997 | Lichtenstein et al. |
| 5,595,909 A | 1/1997 | Hu et al. |
| 5,599,352 A | 2/1997 | Dinh et al. |
| 5,601,595 A | 2/1997 | Smith |
| 5,603,698 A | 2/1997 | Roberts et al. |
| 5,617,854 A | 4/1997 | Munsif |
| 5,626,599 A | 5/1997 | Bourne et al. |
| 5,626,605 A | 5/1997 | Irie et al. |
| 5,632,734 A | 5/1997 | Galel et al. |
| 5,634,474 A | 6/1997 | Grippi |
| 5,634,936 A | 6/1997 | Linden et al. |
| 5,634,942 A | 6/1997 | Chevillon et al. |
| 5,636,644 A | 6/1997 | Hart et al. |
| 5,637,097 A | 6/1997 | Yoon |
| 5,643,320 A | 7/1997 | Lower et al. |
| 5,643,321 A | 7/1997 | McDevitt |
| 5,649,949 A | 7/1997 | Wallace et al. |
| 5,649,950 A | 7/1997 | Bourne et al. |
| 5,653,747 A | 8/1997 | Dereume et al. |
| 5,653,755 A | 8/1997 | Ledergerber |
| 5,669,932 A | 9/1997 | Fischell et al. |
| 5,669,933 A | 9/1997 | Simon et al. |
| 5,672,585 A | 9/1997 | Pierschbacher et al. |
| 5,681,347 A | 10/1997 | Cathcart et al. |
| 5,693,085 A | 12/1997 | Buirge et al. |
| 5,695,518 A | 12/1997 | Laerum |
| 5,695,519 A | 12/1997 | Summers et al. |
| 5,702,421 A | 12/1997 | Schneidt |
| 5,704,910 A | 1/1998 | Humes |
| 5,709,704 A | 1/1998 | Nott et al. |
| 5,709,707 A | 1/1998 | Lock et al. |
| 5,713,853 A | 2/1998 | Clark et al. |
| 5,713,879 A | 2/1998 | Schneider |
| 5,713,921 A | 2/1998 | Bonutti |
| 5,716,408 A | 2/1998 | Eldridge et al. |
| 5,718,717 A | 2/1998 | Bonutti |
| 5,720,764 A | 2/1998 | Naderlinger |
| 5,722,964 A | 3/1998 | Herweck et al. |
| 5,725,552 A | 3/1998 | Kotula et al. |
| 5,728,133 A | 3/1998 | Kontos |
| 5,733,294 A | 3/1998 | Forber et al. |
| 5,733,303 A | 3/1998 | Israel et al. |
| 5,733,325 A | 3/1998 | Robinson et al. |
| 5,735,892 A | 4/1998 | Myers et al. |
| 5,741,297 A | 4/1998 | Simon |
| 5,743,873 A | 4/1998 | Cai et al. |
| 5,755,663 A | 5/1998 | Larsen et al. |
| 5,755,776 A | 5/1998 | Al Saadon |
| 5,755,778 A | 5/1998 | Kleshinski |
| 5,755,781 A | 5/1998 | Jayaraman |
| 5,755,790 A | 5/1998 | Chevillon et al. |
| 5,766,246 A | 6/1998 | Mulhauser et al. |
| 5,772,668 A | 6/1998 | Summers et al. |
| 5,776,142 A | 7/1998 | Gunderson |
| 5,788,661 A | 8/1998 | Japuntich |
| 5,792,179 A | 8/1998 | Sideris |
| 5,795,322 A | 8/1998 | Boudewijn |
| 5,795,325 A | 8/1998 | Valley et al. |
| 5,795,335 A | 8/1998 | Zinreich |
| 5,799,350 A | 9/1998 | Ferek-Petric et al. |
| 5,800,457 A | 9/1998 | Gelbfish |
| 5,800,507 A | 9/1998 | Schwartz |
| 5,800,522 A | 9/1998 | Campbell et al. |
| 5,810,872 A | 9/1998 | Kanesaka et al. |
| 5,824,034 A | 10/1998 | Schmitt et al. |
| 5,827,229 A | 10/1998 | Auth et al. |
| 5,830,224 A | 11/1998 | Cohn et al. |
| 5,836,962 A | 11/1998 | Gianotti |
| 5,836,964 A | 11/1998 | Richter et al. |
| 5,836,969 A | 11/1998 | Kim et al. |
| 5,843,167 A | 12/1998 | Dwyer et al. |
| 5,843,171 A | 12/1998 | Campbell et al. |
| 5,843,176 A | 12/1998 | Weier |
| 5,846,261 A | 12/1998 | Kotula et al. |
| 5,849,004 A | 12/1998 | Bramlet |
| 5,849,034 A | 12/1998 | Schwartz |
| 5,853,420 A | 12/1998 | Chevillon et al. |
| 5,853,422 A | 12/1998 | Huebsch et al. |
| 5,860,998 A | 1/1999 | Robinson et al. |
| 5,861,003 A | 1/1999 | Latson et al. |
| 5,871,693 A | 2/1999 | Lindsay |
| 5,873,906 A | 2/1999 | Lau et al. |
| 5,873,907 A | 2/1999 | Frantzen |
| 5,876,432 A | 3/1999 | Lau et al. |
| 5,879,366 A | 3/1999 | Shaw et al. |
| 5,882,340 A | 3/1999 | Yoon |
| 5,882,351 A | 3/1999 | Fox |
| 5,893,869 A | 4/1999 | Barnhart et al. |
| 5,893,887 A | 4/1999 | Jayaraman |
| 5,895,398 A | 4/1999 | Wensel et al. |
| 5,902,333 A | 5/1999 | Roberts et al. |
| 5,904,703 A | 5/1999 | Gilson |
| 5,907,893 A | 6/1999 | Zadno Azizi et al. |
| 5,908,447 A | 6/1999 | Schroeppel et al. |
| 5,910,129 A | 6/1999 | Koblish et al. |
| 5,925,061 A | 7/1999 | Ogi et al. |
| 5,925,074 A | 7/1999 | Gingras et al. |
| 5,928,261 A | 7/1999 | Ruiz |
| 5,928,269 A | 7/1999 | Alt |
| 5,938,683 A | 8/1999 | Lefebvre |
| 5,941,896 A | 8/1999 | Kerr |
| 5,947,995 A | 9/1999 | Samuels et al. |
| 5,954,741 A | 9/1999 | Fox |
| 5,954,743 A | 9/1999 | Jang |
| 5,954,767 A | 9/1999 | Pajotin et al. |
| 5,957,940 A | 9/1999 | Tanner et al. |
| 5,957,977 A | 9/1999 | Melvin |
| 5,965,089 A | 10/1999 | Jarvik et al. |
| 5,967,976 A | 10/1999 | Larsen et al. |
| 5,968,053 A | 10/1999 | Revelas |
| 5,968,071 A | 10/1999 | Chevillon et al. |
| 5,976,172 A | 11/1999 | Homsma et al. |
| 5,980,558 A | 11/1999 | Wiley |
| 5,980,564 A | 11/1999 | Stinson |
| 5,984,917 A | 11/1999 | Fleischman et al. |
| 5,984,947 A | 11/1999 | Smith |
| 5,986,169 A | 11/1999 | Gjunter |
| 5,991,657 A | 11/1999 | Kim |
| 6,001,118 A | 12/1999 | Daniel et al. |
| 6,007,558 A | 12/1999 | Ravenscroft et al. |
| 6,013,093 A | 1/2000 | Nott et al. |
| 6,024,096 A | 2/2000 | Buckberg |
| 6,024,756 A | 2/2000 | Huebsch et al. |
| 6,042,597 A | 3/2000 | Kveen et al. |
| 6,046,381 A | 4/2000 | Mucke et al. |
| 6,048,329 A | 4/2000 | Thompson et al. |
| 6,051,014 A | 4/2000 | Jang |
| 6,053,932 A | 4/2000 | Daniel et al. |
| 6,059,825 A | 5/2000 | Hobbs et al. |
| 6,068,645 A | 5/2000 | Tu |
| 6,071,279 A | 6/2000 | Whayne et al. |
| 6,077,281 A | 6/2000 | Das |
| 6,077,291 A | 6/2000 | Das |
| 6,080,178 A | 6/2000 | Meglin |
| 6,080,182 A | 6/2000 | Shaw et al. |
| 6,090,096 A | 7/2000 | St. Goar et al. |
| 6,090,097 A | 7/2000 | Barbut et al. |
| 6,090,127 A | 7/2000 | Globerman |
| 6,099,493 A | 8/2000 | Swisher |
| 6,099,549 A | 8/2000 | Bosma et al. |
| 6,117,105 A | 9/2000 | Bresnaham et al. |
| 6,120,539 A | 9/2000 | Eldridge et al. |
| 6,123,715 A | 9/2000 | Amplatz |

(56) References Cited

U.S. PATENT DOCUMENTS

| | | |
|---|---|---|
| 6,123,723 A | 9/2000 | Konya et al. |
| 6,129,755 A | 10/2000 | Mathis et al. |
| 6,142,987 A | 11/2000 | Tsugita |
| 6,146,404 A | 11/2000 | Kim et al. |
| 6,152,946 A | 11/2000 | Broome et al. |
| 6,171,328 B1 | 1/2001 | Addis |
| 6,171,329 B1 | 1/2001 | Shaw et al. |
| 6,174,322 B1 | 1/2001 | Schneidt |
| 6,193,745 B1 | 2/2001 | Fogarty et al. |
| 6,200,276 B1 | 3/2001 | Biesel et al. |
| 6,206,888 B1 | 3/2001 | Bicek et al. |
| 6,214,020 B1 | 4/2001 | Mulhauser et al. |
| 6,214,025 B1 | 4/2001 | Thistle et al. |
| 6,214,029 B1 | 4/2001 | Thill et al. |
| 6,217,600 B1 | 4/2001 | DiMatteo |
| 6,221,092 B1 | 4/2001 | Koike et al. |
| 6,231,581 B1 | 5/2001 | Shank et al. |
| 6,231,589 B1 | 5/2001 | Wessman et al. |
| 6,234,995 B1 | 5/2001 | Peacock, III |
| 6,235,044 B1 | 5/2001 | Root et al. |
| 6,238,416 B1 | 5/2001 | Sideris |
| 6,241,727 B1 | 6/2001 | Tu et al. |
| 6,241,738 B1 | 6/2001 | Dereume et al. |
| 6,241,757 B1 | 6/2001 | An et al. |
| 6,245,012 B1 | 6/2001 | Kleshinski |
| 6,245,103 B1 | 6/2001 | Stinson |
| 6,251,122 B1 | 6/2001 | Tsukernik |
| 6,254,612 B1 | 7/2001 | Hieshima |
| 6,258,026 B1 | 7/2001 | Ravenscroft et al. |
| 6,258,124 B1 | 7/2001 | Darois et al. |
| 6,261,318 B1 | 7/2001 | Lee et al. |
| 6,264,654 B1 | 7/2001 | Swartz et al. |
| 6,264,690 B1 | 7/2001 | Von Oepen |
| 6,267,747 B1 | 7/2001 | Samson et al. |
| 6,267,772 B1 | 7/2001 | Mulhauser et al. |
| 6,267,776 B1 | 7/2001 | O'Connell |
| 6,267,777 B1 | 7/2001 | Bosma et al. |
| 6,270,515 B1 | 8/2001 | Linden et al. |
| 6,273,901 B1 | 8/2001 | Whitcher et al. |
| 6,277,139 B1 | 8/2001 | Levinson et al. |
| 6,280,413 B1 | 8/2001 | Clark et al. |
| 6,287,335 B1 | 9/2001 | Drasler et al. |
| 6,311,692 B1 | 11/2001 | Vaska et al. |
| 6,325,815 B1 | 12/2001 | Kusleika et al. |
| 6,328,755 B1 | 12/2001 | Marshall |
| 6,331,183 B1 | 12/2001 | Suon |
| 6,334,864 B1 | 1/2002 | Amplatz et al. |
| 6,336,938 B1 | 1/2002 | Kavteladze et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,053 B1 | 2/2002 | Boneau |
| 6,352,552 B1 | 3/2002 | Levinson et al. |
| 6,355,052 B1 | 3/2002 | Neuss et al. |
| 6,358,230 B1 | 3/2002 | Davey |
| 6,361,545 B1 | 3/2002 | Macoviak et al. |
| 6,361,546 B1 | 3/2002 | Khosravi |
| 6,371,969 B1 | 4/2002 | Tsugita et al. |
| 6,371,971 B1 | 4/2002 | Tsugita et al. |
| 6,379,368 B1 | 4/2002 | Corcoran et al. |
| 6,391,044 B1 | 5/2002 | Yadav et al. |
| 6,398,792 B1 | 6/2002 | O'Connor |
| 6,402,736 B1 | 6/2002 | Brown et al. |
| 6,416,293 B1 | 7/2002 | Bouchard et al. |
| 6,422,397 B1 | 7/2002 | Lynn et al. |
| 6,428,559 B1 | 8/2002 | Johnson |
| 6,436,112 B2 | 8/2002 | Wensel et al. |
| 6,436,120 B1 | 8/2002 | Meglin |
| 6,436,121 B1 | 8/2002 | Blom |
| 6,440,077 B1 | 8/2002 | Jung et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,451,257 B1 | 9/2002 | Flamer |
| 6,454,775 B1 | 9/2002 | Demarais et al. |
| 6,461,370 B1 | 10/2002 | Gray et al. |
| 6,468,299 B2 | 10/2002 | Stack et al. |
| 6,468,303 B1 | 10/2002 | Amplatz et al. |
| 6,482,222 B1 | 11/2002 | Bruckheimer et al. |
| 6,485,497 B2 | 11/2002 | Wensel et al. |
| 6,485,502 B2 | 11/2002 | Don Michael et al. |
| 6,488,692 B1 | 12/2002 | Spence et al. |
| 6,491,712 B1 | 12/2002 | O'Connor |
| 6,497,709 B1 | 12/2002 | Heath |
| 6,506,204 B2 | 1/2003 | Mazzocchi |
| 6,506,205 B2 | 1/2003 | Goldberg et al. |
| 6,506,408 B1 | 1/2003 | Palasis |
| 6,508,777 B1 | 1/2003 | Macoviak et al. |
| 6,508,782 B1 | 1/2003 | Evans et al. |
| 6,508,833 B2 | 1/2003 | Pavcnik et al. |
| 6,517,559 B1 | 2/2003 | O'Connell |
| 6,517,573 B1 | 2/2003 | Pollock et al. |
| 6,527,962 B1 | 3/2003 | Nadal |
| 6,533,805 B1 | 3/2003 | Jervis |
| 6,534,035 B1 | 3/2003 | Reed |
| 6,537,300 B2 | 3/2003 | Girton |
| 6,540,767 B1 | 4/2003 | Walak et al. |
| 6,540,768 B1 | 4/2003 | Diaz et al. |
| 6,544,167 B2 | 4/2003 | Buckberg et al. |
| 6,544,279 B1 | 4/2003 | Hopkins et al. |
| 6,544,280 B1 | 4/2003 | Daniel et al. |
| 6,547,754 B1 | 4/2003 | Evans et al. |
| 6,551,303 B1 | 4/2003 | Van Tassel et al. |
| 6,551,344 B2 | 4/2003 | Thill |
| 6,562,064 B1 | 5/2003 | deBeer |
| 6,562,071 B2 | 5/2003 | Jarvinen |
| 6,576,001 B2 | 6/2003 | Werneth et al. |
| 6,579,308 B1 | 6/2003 | Jansen et al. |
| 6,582,447 B1 | 6/2003 | Patel et al. |
| 6,585,689 B1 | 7/2003 | Macoviak et al. |
| 6,585,756 B1 | 7/2003 | Strecker |
| 6,585,758 B1 | 7/2003 | Chouinard et al. |
| 6,592,546 B1 | 7/2003 | Barbut et al. |
| 6,596,011 B2 | 7/2003 | Johnson et al. |
| 6,596,013 B2 | 7/2003 | Yang et al. |
| 6,599,314 B2 | 7/2003 | Mathis |
| 6,602,272 B2 | 8/2003 | Boylan et al. |
| 6,602,281 B1 | 8/2003 | Klein |
| 6,605,074 B2 | 8/2003 | Zadno-Azizi et al. |
| 6,605,102 B1 | 8/2003 | Mazzocchi et al. |
| 6,605,110 B2 | 8/2003 | Harrison |
| 6,610,006 B1 | 8/2003 | Amid et al. |
| 6,610,085 B1 | 8/2003 | Lazarus |
| 6,613,076 B1 | 9/2003 | Cherif-Cheikh |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,684 B1 | 9/2003 | Vidlund et al. |
| 6,623,448 B2 | 9/2003 | Slater |
| 6,623,506 B2 | 9/2003 | McGuckin, Jr. et al. |
| 6,623,507 B2 | 9/2003 | Saleh |
| 6,626,899 B2 | 9/2003 | Houser et al. |
| 6,626,937 B1 | 9/2003 | Cox |
| 6,635,070 B2 | 10/2003 | Leeflang et al. |
| 6,638,259 B1 | 10/2003 | Palasis et al. |
| 6,645,143 B2 | 11/2003 | Vantassel et al. |
| 6,645,152 B1 | 11/2003 | Jung et al. |
| 6,645,202 B1 | 11/2003 | Pless et al. |
| 6,645,225 B1 | 11/2003 | Atkinson |
| 6,652,554 B1 | 11/2003 | Wholey et al. |
| 6,652,555 B1 | 11/2003 | VanTassel et al. |
| 6,652,556 B1 | 11/2003 | VanTassel et al. |
| 6,656,203 B2 | 12/2003 | Roth et al. |
| 6,656,206 B2 | 12/2003 | Corcoran et al. |
| 6,656,220 B1 * | 12/2003 | Gomez et al. ............... 623/1.15 |
| 6,656,221 B2 | 12/2003 | Taylor et al. |
| 6,660,021 B1 | 12/2003 | Palmer et al. |
| 6,660,031 B2 | 12/2003 | Tran et al. |
| 6,663,606 B1 | 12/2003 | Barry et al. |
| 6,663,651 B2 | 12/2003 | Krolik et al. |
| 6,669,708 B1 | 12/2003 | Nissenbaum et al. |
| 6,673,102 B1 | 1/2004 | Vonesh et al. |
| 6,676,666 B2 | 1/2004 | Vrba et al. |
| 6,676,682 B1 | 1/2004 | Tsugita et al. |

(56) References Cited

U.S. PATENT DOCUMENTS

| | | |
|---|---|---|
| 6,682,505 B2 | 1/2004 | Bates et al. |
| 6,682,554 B2 | 1/2004 | Oepen et al. |
| 6,685,738 B2 | 2/2004 | Chouinard et al. |
| 6,689,150 B1 | 2/2004 | VanTassel et al. |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,694,983 B2 | 2/2004 | Wolf et al. |
| 6,695,858 B1 | 2/2004 | Dubrul et al. |
| 6,695,864 B2 | 2/2004 | Macoviak et al. |
| 6,699,278 B2 | 3/2004 | Fischell et al. |
| 6,702,835 B2 | 3/2004 | Ginn |
| 6,706,065 B2 | 3/2004 | Langberg et al. |
| 6,709,442 B2 | 3/2004 | Miller et al. |
| 6,712,834 B2 | 3/2004 | Yassour et al. |
| 6,712,835 B2 | 3/2004 | Mazzocchi et al. |
| 6,712,836 B1 | 3/2004 | Berg et al. |
| 6,716,238 B2 | 4/2004 | Elliott |
| 6,723,133 B1 | 4/2004 | Pajotin |
| 6,726,701 B2 | 4/2004 | Gilson et al. |
| 6,726,703 B2 | 4/2004 | Broome et al. |
| 6,731,982 B1 | 5/2004 | Kroll et al. |
| 6,736,823 B2 | 5/2004 | Darois et al. |
| 6,736,839 B2 | 5/2004 | Cummings |
| 6,736,854 B2 | 5/2004 | Vadurro et al. |
| 6,740,061 B1 | 5/2004 | Oslund et al. |
| 6,740,094 B2 | 5/2004 | Maitland et al. |
| 6,740,112 B2 | 5/2004 | Yodfat et al. |
| 6,740,122 B1 | 5/2004 | Pajotin |
| 6,749,629 B1 | 6/2004 | Hong et al. |
| 6,752,825 B2 | 6/2004 | Eskuri |
| 6,754,528 B2 | 6/2004 | Bardy et al. |
| 6,754,531 B1 | 6/2004 | Kroll et al. |
| 6,755,846 B1 | 6/2004 | Yadav |
| 6,755,847 B2 | 6/2004 | Eskuri |
| 6,756,094 B1 | 6/2004 | Wang et al. |
| 6,758,830 B1 | 7/2004 | Schaer et al. |
| 6,761,731 B2 | 7/2004 | Majercak |
| 6,764,510 B2 | 7/2004 | Vidlund et al. |
| 6,766,196 B1 | 7/2004 | Kroll et al. |
| 6,776,770 B1 | 8/2004 | Trerotola |
| 6,776,784 B2 | 8/2004 | Ginn |
| 6,776,793 B2 * | 8/2004 | Brown et al. ................ 623/1.15 |
| 6,780,183 B2 | 8/2004 | Jimenez, Jr. et al. |
| 6,783,499 B2 | 8/2004 | Schwartz |
| 6,783,538 B2 | 8/2004 | McGuckin, Jr. et al. |
| 6,790,213 B2 | 9/2004 | Cherok et al. |
| 6,790,218 B2 | 9/2004 | Jayaraman |
| 6,790,230 B2 | 9/2004 | Beyersdorf et al. |
| 6,790,231 B2 | 9/2004 | Liddicoat et al. |
| 6,793,666 B2 | 9/2004 | Hansen et al. |
| 6,795,731 B1 | 9/2004 | Kroll et al. |
| 6,797,083 B2 | 9/2004 | Peterson |
| 6,799,357 B2 | 10/2004 | Webb et al. |
| 6,805,128 B1 | 10/2004 | Pless et al. |
| 6,805,129 B1 | 10/2004 | Pless et al. |
| 6,805,711 B2 | 10/2004 | Quijano et al. |
| 6,808,537 B2 | 10/2004 | Michelson |
| 6,827,731 B2 | 12/2004 | Armstrong et al. |
| 6,835,378 B2 | 12/2004 | Davis et al. |
| 6,840,950 B2 | 1/2005 | Stanford et al. |
| 6,843,798 B2 | 1/2005 | Kusleika et al. |
| 6,849,084 B2 | 2/2005 | Rabkin et al. |
| 6,866,662 B2 | 3/2005 | Fuimaono et al. |
| 6,866,680 B2 | 3/2005 | Yassour et al. |
| 6,878,162 B2 | 4/2005 | Bales et al. |
| 6,881,218 B2 | 4/2005 | Beyer et al. |
| 6,887,214 B1 | 5/2005 | Levin et al. |
| 6,887,257 B2 | 5/2005 | Salahieh et al. |
| 6,887,268 B2 | 5/2005 | Butaric et al. |
| 6,890,353 B2 | 5/2005 | Cohn et al. |
| 6,895,265 B2 | 5/2005 | Silver |
| 6,899,727 B2 | 5/2005 | Armstrong et al. |
| 6,902,572 B2 | 6/2005 | Beulke et al. |
| 6,905,479 B1 | 6/2005 | Bouchard et al. |
| 6,907,286 B1 | 6/2005 | Kroll et al. |
| 6,911,037 B2 | 6/2005 | Gainor et al. |
| 6,913,614 B2 | 7/2005 | Marino et al. |
| 6,913,622 B2 | 7/2005 | Gjunter |
| 6,929,633 B2 | 8/2005 | Evans et al. |
| 6,929,660 B1 | 8/2005 | Ainsworth et al. |
| 6,931,280 B1 | 8/2005 | Yang |
| 6,939,361 B1 | 9/2005 | Kleshinski |
| 6,942,635 B2 | 9/2005 | Rosenblatt et al. |
| 6,951,570 B2 | 10/2005 | Linder et al. |
| 6,955,688 B2 | 10/2005 | Wilson et al. |
| 6,962,598 B2 | 11/2005 | Linder et al. |
| 6,966,886 B2 | 11/2005 | Appling |
| 6,972,025 B2 | 12/2005 | WasDyke |
| 6,974,469 B2 | 12/2005 | Broome et al. |
| 6,976,967 B2 | 12/2005 | Dahl et al. |
| 6,988,983 B2 | 1/2006 | Connors et al. |
| 6,989,021 B2 | 1/2006 | Bosma et al. |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,004,964 B2 | 2/2006 | Thompson et al. |
| 7,011,671 B2 | 3/2006 | Welch |
| 7,012,106 B2 | 3/2006 | Yuan et al. |
| 7,014,765 B2 | 3/2006 | Dannenmaier |
| 7,052,487 B2 | 5/2006 | Cohn et al. |
| 7,052,500 B2 | 5/2006 | Bashiri et al. |
| 7,052,511 B2 | 5/2006 | Weldon et al. |
| 7,056,286 B2 | 6/2006 | Ravenscroft et al. |
| 7,056,336 B2 | 6/2006 | Armstrong et al. |
| 7,060,082 B2 | 6/2006 | Goll et al. |
| 7,063,682 B1 | 6/2006 | Whayne et al. |
| 7,066,951 B2 | 6/2006 | Chobotov |
| 7,083,633 B2 | 8/2006 | Morrill et al. |
| 7,087,069 B2 | 8/2006 | Petrovic et al. |
| 7,094,249 B1 | 8/2006 | Broome et al. |
| 7,112,219 B2 | 9/2006 | Vidlund et al. |
| 7,122,034 B2 | 10/2006 | Belhe et al. |
| 7,122,049 B2 | 10/2006 | Banas et al. |
| 7,125,420 B2 | 10/2006 | Rourke et al. |
| 7,131,966 B1 | 11/2006 | Tamari |
| 7,131,993 B2 | 11/2006 | Gregorich |
| 7,137,991 B2 | 11/2006 | Fedie |
| 7,137,993 B2 | 11/2006 | Acosta et al. |
| 7,147,649 B2 | 12/2006 | Thomas |
| 7,149,587 B2 | 12/2006 | Wardle et al. |
| 7,152,452 B2 | 12/2006 | Kokish |
| 7,163,553 B2 | 1/2007 | Limon |
| 7,169,165 B2 | 1/2007 | Belef et al. |
| 7,179,274 B2 | 2/2007 | Bruckheimer et al. |
| 7,179,275 B2 | 2/2007 | McGuckin, Jr. et al. |
| 7,179,291 B2 | 2/2007 | Rourke et al. |
| 7,181,261 B2 | 2/2007 | Silver et al. |
| 7,186,262 B2 | 3/2007 | Saadat |
| 7,186,264 B2 | 3/2007 | Liddicoat et al. |
| 7,189,203 B2 | 3/2007 | Lau et al. |
| 7,192,434 B2 | 3/2007 | Anderson et al. |
| 7,209,783 B2 | 4/2007 | Fellows et al. |
| 7,214,237 B2 | 5/2007 | Don Michael et al. |
| 7,220,271 B2 | 5/2007 | Clubb et al. |
| 7,226,464 B2 | 6/2007 | Garner et al. |
| 7,229,462 B2 | 6/2007 | Sutton et al. |
| 7,229,469 B1 | 6/2007 | Witzel et al. |
| 7,231,260 B2 | 6/2007 | Wallace et al. |
| 7,232,453 B2 | 6/2007 | Shimon |
| 7,241,257 B1 | 7/2007 | Ainsworth et al. |
| 7,241,310 B2 | 7/2007 | Taylor et al. |
| 7,250,049 B2 | 7/2007 | Roop et al. |
| 7,252,679 B2 | 8/2007 | Fischell et al. |
| 7,258,697 B1 | 8/2007 | Cox et al. |
| 7,285,119 B2 | 10/2007 | Stewart et al. |
| 7,294,214 B2 | 11/2007 | Craig |
| 7,294,311 B2 | 11/2007 | Coville |
| 7,303,560 B2 | 12/2007 | Chin et al. |
| 7,306,618 B2 | 12/2007 | Demond et al. |
| 7,306,622 B2 | 12/2007 | Jones et al. |
| 7,309,354 B2 | 12/2007 | Mathis et al. |
| 7,316,708 B2 | 1/2008 | Gordon et al. |

(56) References Cited

U.S. PATENT DOCUMENTS

| | | | |
|---|---|---|---|
| 7,319,035 B2 | 1/2008 | Vacanti et al. |
| 7,323,001 B2 | 1/2008 | Clubb et al. |
| 7,323,002 B2 | 1/2008 | Johnson et al. |
| 7,323,003 B2 | 1/2008 | Lowe |
| 7,329,269 B2 | 2/2008 | Shapiro et al. |
| 7,331,976 B2 | 2/2008 | McGuckin, Jr. et al. |
| 7,331,992 B2 | 2/2008 | Randall et al. |
| 7,338,512 B2 | 3/2008 | McGuckin, Jr. et al. |
| 7,344,553 B2 | 3/2008 | Opolski et al. |
| 7,344,560 B2 | 3/2008 | Gregorich et al. |
| 7,351,259 B2 | 4/2008 | Swinford et al. |
| 7,357,812 B2 | 4/2008 | Andreas et al. |
| 7,359,752 B1 | 4/2008 | Bornzin et al. |
| 7,363,082 B2 | 4/2008 | Ransbury et al. |
| 7,364,588 B2 | 4/2008 | Mathis et al. |
| 7,399,308 B2 | 7/2008 | Borillo et al. |
| 7,431,691 B1 | 10/2008 | Wilk |
| 7,445,630 B2 | 11/2008 | Lashinski et al. |
| 7,452,371 B2 | 11/2008 | Pavcnik et al. |
| 7,520,890 B2 | 4/2009 | Phillips |
| 7,556,644 B2 | 7/2009 | Burpee |
| 7,594,927 B2 | 9/2009 | Majercak et al. |
| 7,604,870 B2 | 10/2009 | Chernyshov et al. |
| 7,611,531 B2 | 11/2009 | Calisse |
| 7,722,661 B2 | 5/2010 | Lenz et al. |
| 7,883,538 B2 | 2/2011 | To et al. |
| 2001/0039434 A1 | 11/2001 | Frazier |
| 2001/0044650 A1 | 11/2001 | Simso et al. |
| 2002/0045935 A1 | 4/2002 | Jang |
| 2002/0082682 A1 | 6/2002 | Barclay et al. |
| 2002/0120323 A1 | 8/2002 | Thompson et al. |
| 2002/0169474 A1 | 11/2002 | Kusleika et al. |
| 2002/0183787 A1 | 12/2002 | Wahr et al. |
| 2003/0004567 A1* | 1/2003 | Boyle .................. A61F 2/915 623/1.16 |
| 2003/0028213 A1 | 2/2003 | Thill et al. |
| 2003/0040771 A1 | 2/2003 | Hyodoh et al. |
| 2003/0097172 A1 | 5/2003 | Shalev et al. |
| 2003/0109887 A1 | 6/2003 | Galdonik et al. |
| 2003/0114920 A1 | 6/2003 | Caro et al. |
| 2003/0130726 A1 | 7/2003 | Thorpe et al. |
| 2003/0144694 A1 | 7/2003 | Chanduszko et al. |
| 2003/0167068 A1 | 9/2003 | Amplatz |
| 2003/0191495 A1 | 10/2003 | Ryan et al. |
| 2003/0195555 A1 | 10/2003 | Khairkhahan et al. |
| 2003/0195609 A1 | 10/2003 | Berenstein et al. |
| 2003/0199923 A1 | 10/2003 | Khairkhahan et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0006381 A1 | 1/2004 | Sequin et al. |
| 2004/0039442 A1 | 2/2004 | St. Goar et al. |
| 2004/0073242 A1 | 4/2004 | Chanduszko |
| 2004/0088044 A1 | 5/2004 | Brown et al. |
| 2004/0092973 A1 | 5/2004 | Chanduszko et al. |
| 2004/0093017 A1 | 5/2004 | Chanduszko |
| 2004/0102807 A1 | 5/2004 | Kusleika et al. |
| 2004/0133236 A1 | 7/2004 | Chanduszko |
| 2004/0147997 A1 | 7/2004 | Gittings |
| 2004/0158247 A1 | 8/2004 | Sitiso et al. |
| 2004/0158312 A1 | 8/2004 | Chouinard et al. |
| 2004/0167609 A1 | 8/2004 | Majercak |
| 2004/0176799 A1 | 9/2004 | Chanduszko et al. |
| 2004/0186556 A1 | 9/2004 | Hogendijk et al. |
| 2004/0186560 A1 | 9/2004 | Alt |
| 2004/0204752 A1 | 10/2004 | Ehr et al. |
| 2004/0215219 A1 | 10/2004 | Eldridge |
| 2004/0220585 A1 | 11/2004 | Nikolchev |
| 2004/0249408 A1 | 12/2004 | Murphy et al. |
| 2004/0267191 A1 | 12/2004 | Gifford, III et al. |
| 2004/0267306 A1 | 12/2004 | Blaeser et al. |
| 2004/0267350 A1* | 12/2004 | Roubin .................. A61F 2/91 623/1.15 |
| 2005/0015136 A1 | 1/2005 | Lkeuchi et al. |
| 2005/0043759 A1 | 2/2005 | Chanduszko |
| 2005/0055080 A1 | 3/2005 | Istephanous et al. |
| 2005/0090857 A1 | 4/2005 | Kusleika et al. |
| 2005/0090858 A1 | 4/2005 | Pavlovic |
| 2005/0107863 A1 | 5/2005 | Brown |
| 2005/0131451 A1 | 6/2005 | Kleshinski et al. |
| 2005/0131516 A1 | 6/2005 | Greenhalgh |
| 2005/0192620 A1 | 9/2005 | Cully et al. |
| 2005/0192626 A1 | 9/2005 | Widomski et al. |
| 2005/0192654 A1 | 9/2005 | Chanduszko et al. |
| 2005/0197186 A1 | 9/2005 | Ohta |
| 2005/0197187 A1 | 9/2005 | Mitsuyoshi et al. |
| 2005/0216054 A1 | 9/2005 | Widomski et al. |
| 2005/0288764 A1 | 12/2005 | Snow et al. |
| 2006/0015137 A1 | 1/2006 | WasDyke |
| 2006/0020322 A1 | 1/2006 | Leynov et al. |
| 2006/0106452 A1 | 5/2006 | Niermann |
| 2006/0116751 A1 | 6/2006 | Bayle et al. |
| 2006/0142849 A1* | 6/2006 | Killion et al. .............. 623/1.31 |
| 2006/0247759 A1 | 11/2006 | Burpee et al. |
| 2007/0055348 A1 | 3/2007 | Pryor |
| 2007/0129786 A1 | 6/2007 | Beach et al. |
| 2007/0185563 A1 | 8/2007 | Zarbatany et al. |
| 2007/0198050 A1 | 8/2007 | Ravenscroft et al. |
| 2007/0219618 A1 | 9/2007 | Cully et al. |
| 2007/0232981 A1 | 10/2007 | Ravenscroft et al. |
| 2007/0255387 A1 | 11/2007 | Kramer et al. |
| 2008/0103584 A1 | 5/2008 | Su et al. |
| 2008/0109068 A1 | 5/2008 | Fischell et al. |
| 2008/0125849 A1 | 5/2008 | Burpee et al. |
| 2008/0208319 A1 | 8/2008 | Rabkin et al. |
| 2008/0215129 A1 | 9/2008 | Venturelli et al. |
| 2008/0294240 A1 | 11/2008 | Casey |
| 2008/0306581 A1 | 12/2008 | Berglund et al. |
| 2009/0024205 A1 | 1/2009 | Hebert et al. |
| 2009/0036976 A1 | 2/2009 | Beach et al. |
| 2009/0099592 A1 | 4/2009 | Buiser et al. |
| 2009/0118810 A1 | 5/2009 | Klein et al. |
| 2009/0163989 A1 | 6/2009 | Contiliano et al. |
| 2009/0182407 A1 | 7/2009 | Leanna et al. |
| 2009/0210049 A1 | 8/2009 | Thielen et al. |
| 2009/0264978 A1 | 10/2009 | Dieck et al. |
| 2010/0004730 A1 | 1/2010 | Benjamin et al. |
| 2010/0023106 A1 | 1/2010 | Meyer et al. |
| 2010/0057187 A1 | 3/2010 | Caldarise et al. |
| 2010/0076545 A1 | 3/2010 | Kleshinski et al. |
| 2010/0137973 A1 | 6/2010 | Sutermeister |
| 2010/0222772 A1 | 9/2010 | Kleshinski et al. |
| 2010/0294287 A1 | 11/2010 | Raju et al. |
| 2011/0251671 A1 | 10/2011 | Heraty et al. |
| 2011/0301685 A1 | 12/2011 | Kao |
| 2011/0307049 A1 | 12/2011 | Kao |
| 2012/0078341 A1 | 3/2012 | Kao |
| 2012/0078344 A1 | 3/2012 | Kao |

FOREIGN PATENT DOCUMENTS

| | | | |
|---|---|---|---|
| EP | 0335341 B1 | 3/1992 |
| EP | 0541063 A2 | 5/1993 |
| EP | 0621016 A1 | 10/1993 |
| EP | 0657147 A2 | 6/1995 |
| EP | 0701800 A1 | 3/1996 |
| EP | 0962194 A2 | 12/1999 |
| EP | 1050265 A2 | 11/2000 |
| EP | 1304091 A2 * | 4/2003 | .............. A61F 2/06 |
| EP | 1917931 A2 | 5/2008 |
| JP | 06189971 A2 | 7/1994 |
| JP | 06343703 A2 | 12/1994 |
| JP | 07265339 A2 | 10/1995 |
| JP | 08089585 A2 | 4/1996 |
| JP | 08215200 | 8/1996 |
| JP | 08257031 | 10/1996 |
| JP | 08299456 A2 | 11/1996 |
| JP | 2000126304 A | 5/2000 |
| JP | 2002119516 A | 4/2002 |
| JP | 2002525183 | 8/2002 |
| JP | 2002355248 A | 12/2002 |
| JP | 2003521308 | 7/2003 |
| JP | 2003521988 | 7/2003 |
| WO | WO97/13463 A1 | 4/1997 |

(56) References Cited

FOREIGN PATENT DOCUMENTS

| WO | WO 98/38945 A1 | 9/1998 |
|---|---|---|
| WO | WO 99/44540 A2 | 9/1999 |
| WO | WO 00/16718 A1 | 3/2000 |
| WO | WO 00/28922 A1 | 5/2000 |
| WO | WO 00/57813 A1 | 10/2000 |
| WO | WO 03/051425 A2 | 6/2003 |
| WO | WO03/101312 A1 | 12/2003 |
| WO | WO2007/040249 | 4/2007 |
| WO | WO 2007/092276 A2 | 8/2007 |
| WO | WO2008/060345 A1 | 5/2008 |
| WO | WO2011/053737 A2 | 5/2011 |

OTHER PUBLICATIONS

Malvé et al.; FSI analysis of the coughing mechanism in a human trachea; Annals of Biomedical Engineering; vol. 38; No. 4; pp. 1556-1565; 2010.

Bonsignore et al.; U.S. Appl. No. 13/100,132 entitled "Alternating circumferential bridge stent design and methods for use therof," filed May 3, 2011.

Boston Scientific Corp.; Ultraflex Tracheobronchial Stent System (prod. info.); www.bostonscientific.com/templatedata/imports/collateral/PulmonaryEndoscopy/prospec_ultrixtb_01_us.pdf; 2 pgs.; 2007 (pub. year sufficiently earlier than eff. US filing date & any foreign priority date).

Raju et al.; U.S. Appl. No. 11/944,094 entitled "Venous Stent," filed Nov. 21, 2007.

Raju et al.; U.S. Appl. No. 12/903,056 entitled "Venous Stent," filed Oct. 12, 2010.

Raju et al.; U.S. Appl. No. 12/603,970 entitled "Venous Stent," filed Oct. 22, 2009.

\* cited by examiner

|  | Bridging Element ||||| Z Elements ||||
|---|---|---|---|---|---|---|---|---|---|
|  | Number | Length | Angle | Width | Thickness | Number | Length | Width | Thickness |
| + Axial Flexibility | + | + | + + | - | - | + | - | - | - |
| + Hoop Stiffness | - |  | + | + | + | - | - - | + + | + |
| + Pinching Stiffness | - | + | + | + | + + | - | - - | + | + + |
| - Rotation with Diam | 0 | - | - | 0 | 0 | 0 | 0 | 0 | 0 |
| + Scaffolding performance | + | - | + | 0 | 0 | + | - | 0 | 0 |

ALTERNATING CIRCUMFERENTIAL BRIDGE STENT DESIGN AND METHODS FOR USE THEREOF

CROSS REFERENCE TO RELATED APPLICATIONS

This application claims priority to U.S. Provisional Patent Application No. 61/258,145, filed Nov. 4, 2009 entitled "Stent for Relief of Pelvic Venous Outflow Obstruction and Methods for Use Thereof." This application also claims priority to U.S. Provisional Patent Application No. 61/290,836, filed on Dec. 29, 2009 entitled "Alternating Circumferential Bridge Stent Design and Methods of Use Therefore." This application also claims priority to U.S. Provisional Patent Application No. 61/391,462, filed on Oct. 8, 2010 entitled "Alternative Circumferential Bridge Stent Design and methods of Use Therefore." These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to stents and more particularly to stents having different modules that when combined provide advantages for the physiological challenges posed in particular anatomies.

BACKGROUND OF THE INVENTION

Generally, stents are used as an alternative to surgery to obtain and maintain the patency of a variety of body passageways, while maintaining the integrity of the passageway. The environments of human vasculature and body passageways are characterized by varied, dynamic, and mobile anatomy. Vessels vary from simple to complex shapes, can be uniform in diameter or change abruptly or gradually from one diameter to another, and are subjected to a range of forces exerted by an assortment of anatomical structures surrounding and adjacent to these body passageways. It is critical that stents be designed to accommodate significant variation in the shape and size of body passageways while providing structural support and flexibility as required by particular indications of use.

The primary role of a stent is to provide radial expansion and scaffolding within the affected segment, thereby improving flow and preserving the viability and full function of distal tissues. In performing this primary function, however, a stent must exist in harmony with surrounding structures of the body, including vessels, nerves, muscles, organs, and other tissues. Each region of the anatomy presents a unique combination of loads, interactions, and constraints that will be experienced by the implant. In many regions of the anatomy, these boundary conditions will vary not only with location, but also with time. These temporal variations, including motions associated with the cardiac pulsatile cycle, gait cycle, respiratory cycle, or other dynamic events, are especially important considerations for the durability of the implant itself, as well as the efficacy of the therapy. Consequently, stent designs are needed that can (1) provide adequate outward radial support to remodel the lumen and improve distal perfusion, (2) provide adequate crush recoverability when subjected to compression by the surrounding muscles or external forces, (3) provide adequate flexibility to accommodate localized stretching, compression, bending, or torsion in mobile segments of the artery, (4) provide durability to survive the cyclic motions associated with limb flexion, and (5) provide uniform scaffolding throughout the treatment region, including the local regions adjacent to calcification that may be subjected to highly focal cyclic loading or displacement. These competing demands have proven difficult to resolve with a single design.

SUMMARY OF THE INVENTION

In general, in one aspect, a stent includes a first section and a second section aligned with the first section along a longitudinal axis of the stent. The first section and the second section each include a plurality of expandable modules and a plurality of bridging modules. Each expandable module includes a plurality of strut elements that join together at a plurality of apices. Each bridging module includes bridging elements that connect an apex of a first module with an apex of a second module. The first section is more flexible along the longitudinal axis than the second section and is configured to be placed in a specific region of a vessel that requires flexibility to accommodate surrounding anatomy.

This and other embodiments can include one or more of the following features. The second section can be configured to provide more radial stiffness than the first section and can be configured to be placed in a specific region of the vessel that requires radial stiffness to counteract crushing force caused by surrounding anatomy.

The plurality of bridging modules can be arranged to alternate along the longitudinal axis between clockwise bridging modules and counterclockwise bridging modules the clockwise bridging modules including bridging elements that extend at a clockwise angle with respect to the longitudinal axis, and the counterclockwise bridging modules including bridging elements that extend at a counterclockwise angle with respect to the longitudinal axis. The clockwise bridging modules can be configured to counterbalance any rotation caused by the counterclockwise bridging modules.

There can be a greater number of bridging elements around a circumference of the first section than a circumference of the second section. A length of each bridging element of the first section can be greater than a length of each bridging element of the second section. A pitch of the bridging elements within each bridging module of the first section can be greater than a pitch of the bridging elements within each bridging module of the second section. A width of each bridging element of the first section can be less than a width of each bridging element of the second section. A thickness of each bridging elements of the first section can be less than a thickness of each bridging element of the second section.

There can be a greater number of strut elements around a circumference of the first section than a circumference of the second section. A length of each strut element of the first section can be less than a length of each strut element of the second section. A width of each strut element of the first section can be less than a width of each strut element of the second section. A thickness of each strut element of the first section can be less than a thickness of each strut element of the second section.

The vessel can be a left iliac vein, and the specific region can be proximate to where a left common iliac vein crosses an inguinal ligament. The vessel can be a superficial femoral artery, and the specific region can be between a profunda and an adductor hiatus. The vessel can be a coronary artery, and wherein the specific region can be near a branch vessel. The vessel can be a renal artery, and the specific region can be near an ostium. The vessel can be a carotid artery, and the specific region can be near a carotid sinus. The vessel can further be a trachea, a fistula, or a graft.

In general, in one aspect, a method of inserting a stent includes inserting a stent into a vessel. The stent includes a first section and a second section. The first section is more flexible along a longitudinal axis of the stent than the second section. The first section and the second section each include a plurality of expandable modules and a plurality of bridging modules. Each expandable module includes a plurality of strut elements that join together at a plurality of apices. Each bridging module includes bridging elements that connect an apex of a first module with an apex of a second module. The method further includes aligning the first section with a specific region of the vessel that requires flexibility to accommodate surrounding anatomy.

This and other embodiments can include one or more of the following features. The second section can be configured to provide more radial stiffness than the first section, and the method can further include aligning the second section with a specific region of the vessel that requires radial stiffness to counteract crushing force caused by surrounding anatomy.

The plurality of bridging modules can be arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis.

The vessel can be a left iliac vein, and the specific region can be proximate to where a left common iliac vein crosses an inguinal ligament. The vessel can be a superficial femoral artery, and the specific region can be between a profunda and an adductor hiatus. The vessel can be a coronary artery, and the specific region can be near a branch vessel. The vessel can be a renal artery, and the specific region can be near an ostium. The vessel can be a carotid artery, and the specific region can be near a carotid sinus. The vessel can further be a trachea, a fistula, or a graft.

In general, in one aspect, a stent includes a first section and a second section aligned with the first stent section along a longitudinal axis of the stent. The first section and the second section each include a plurality of expandable modules and a plurality of bridging modules. Each expandable module includes a plurality of strut elements that join together at a plurality of apices. Each bridging module includes bridging elements that connect an apex of a first module with an apex of a second module. The first section is more radially stiff than the second section and is configured to be placed in a specific region of the vessel that requires radial stiffness to counteract crushing force caused by surrounding anatomy.

This and other embodiments can include one or more of the following features. The second section can be more flexible along the longitudinal axis than the first section and can be configured to be placed in a specific region of a vessel that requires flexibility to accommodate surrounding anatomy.

The plurality of bridging modules can be arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis. The clockwise bridging modules can be configured to counterbalance any rotation caused by the counterclockwise bridging modules.

There can be a smaller number of bridging elements around a circumference of the first section than a circumference of the second section. A length of each bridging element of the first section can be greater than a length of each bridging element of the second section. A pitch of the bridging elements within each bridging module of the first section can be greater than a pitch of the bridging elements within each bridging module of the second section. A width of each bridging element of the first section cam be greater than a width of each bridging element of the second section. A thickness of each bridging element of the first section can be greater than a thickness of each bridging element of the second section.

There can be a smaller number of strut elements around a circumference of the first section than a circumference of the second section. A length of each strut element of the first section can be less than a length of each strut element of the second section. A width of each strut element of the first section can be greater than a width of each strut element of the second section. A thickness of each strut element of the first section can be greater than a thickness of each strut element of the second section.

The vessel can be a left iliac vein, and the specific region can be proximate to where a right iliac artery crosses a left common iliac vein. The vessel can be a left iliac vein, and the specific region is proximate to where a left internal iliac artery crosses a left common iliac vein. The vessel can be a superficial femoral artery, and the specific region can be proximate to an inguinal ligament. The vessel can be the superficial femoral artery, and the specific region can be proximate to a Hunters canal. The vessel can be a coronary artery, and the specific region can be distant from a branch vessel. The vessel can be a renal artery, and the specific region can be distant form an ostium. The vessel can be a carotid artery, and the specific region can be distant from a sinus. The vessel can further be a trachea, a fistula, or a graft.

In general, in one aspect, a method of inserting a stent includes inserting a stent into a vessel. The stent includes a first section and a second section. The first section is more radially stiff than the second section. The first section and the second section each include a plurality of expandable modules and a plurality of bridging modules. Each expandable module includes a plurality of strut elements that join together at a plurality of apices. Each bridging module includes bridging elements that connect an apex of a first module with an apex of a second module. The method further includes aligning the first section with a specific region of the vessel that requires radial stiffness to counteract crushing force caused by surrounding anatomy.

The second section can be more axially flexible than the first section, the method further comprising aligning the second section with a specific region of the vessel that requires flexibility to accommodate surrounding anatomy.

The plurality of bridging modules can be arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis.

The vessel can be a left iliac vein, and the specific region can be proximate to where a right iliac artery crosses a left common iliac vein. The vessel can be a left iliac vein, and the specific region is proximate to where a left internal iliac artery crosses a left common iliac vein. The vessel can be a superficial femoral artery, and the specific region can be proximate to an inguinal ligament. The vessel can be the superficial femoral artery, and the specific region can be proximate to a Hunters canal. The vessel can be a coronary artery, and the specific region can be distant from a branch vessel. The vessel can be a renal artery, and the specific region can be distant form an ostium. The vessel can be a carotid artery, and the specific region can be distant from a sinus. The vessel can further be a trachea, a fistula, or a graft.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

FIG. 6C shows a chart of variables vs. module characteristics for the stents described herein.

DETAILED DESCRIPTION OF THE INVENTION

Embodiments of the present invention are directed toward stents having a modular architecture that permits regions of the stent to be specifically tailored to the specific anatomical challenges of the vessel undergoing treatment. While applicable to other portions of the body where compression resistive and/or flexible stents are well suited, the illustrative embodiments described herein are directed at stents designed to resolve obstructive lesions of the pelvic veins, femoral arteries, coronary arteries, renal arteries, carotid arteries, fistulae, and the trachea.

Embodiments of the stent described herein include a combination of a number of different modules. The physical and engineering properties of each module are tailored depending upon the required function of the module with respect to the rest of the stent. Examples of different types of modules include: (1) modules designed to provide radial stiffness to anchor the stent or to resist external compressive forces; and (2) modules configured to provide added flexibility to the stent within the treated vessel in order to maintain patency of the vessel. Stent embodiments according to the present invention include one or more modules that are specifically sized and positioned with respect to one another so as to conform to a specific anatomical position.

Stent Description

Figure 1:
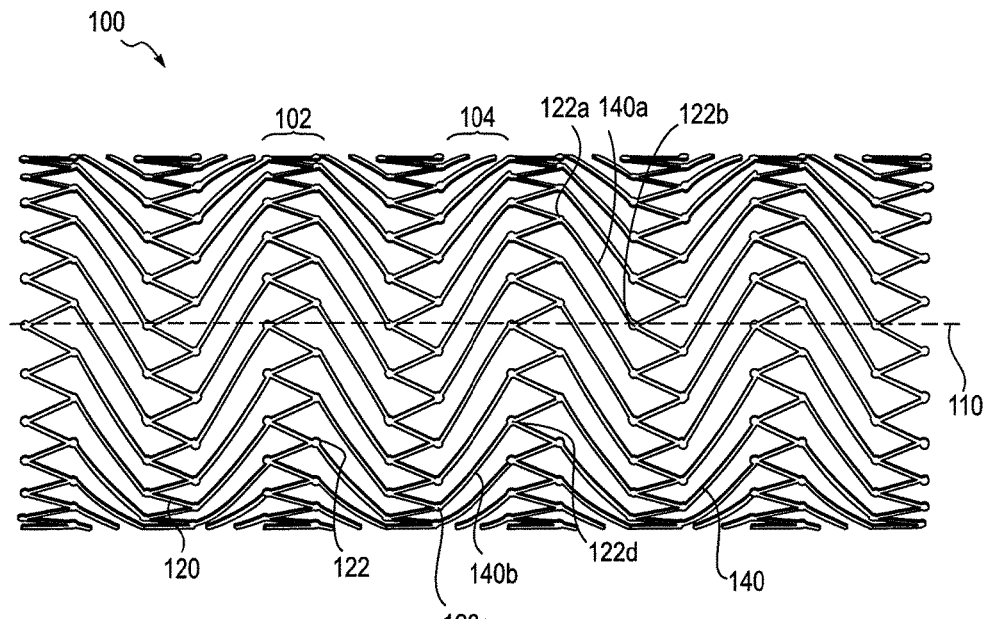
FIG. 1 shows an exemplary stent as described herein.

Referring to FIG. 1, a stent 100 can include a series of expandable ring members 102 connected by bridging members 104. Each expandable ring member 102 can include a series of strut elements 120 disposed around the circumference of the stent 100. Moreover, each bridging member 104 can include circumferential bridging elements 140 connecting the struts 120 of adjacent expandable ring members 102. The pitch of the circumferential bridging elements 140 can alternate between bridging members 104. The number, design, order, and connection of the expandable ring members 102 and bridging members 104 define the overall architecture of the stent 100. The strength, stiffness, flexibility, and inner rotation of the stent can be controlled by the selection and design of these expandable ring members 102 and bridging members 104.

Expandable Ring Members

Figure 2:
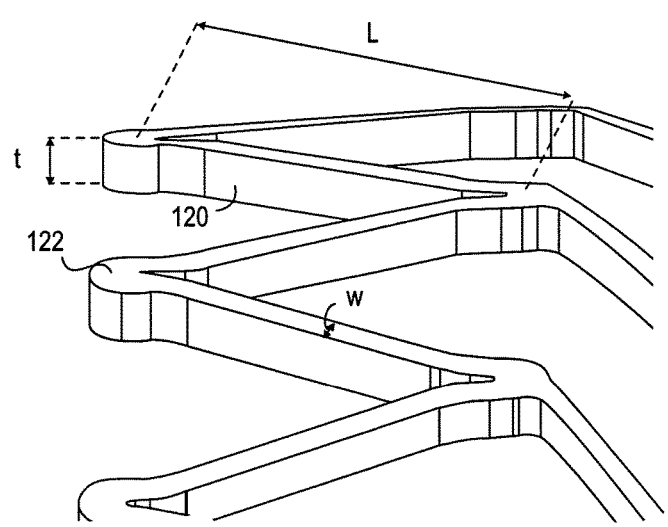
FIG. 2 is a close up of a portion of an expandable ring member described herein.

Referring to FIGS. 1 and 2, the expandable ring members 102 can include a series of struts 120 arranged in a zig-zag shape around the circumference of the stent 100. That is, the struts 120, arranged around the circumference of the stent 100, can connect together at apices 122.

Radial Stiffness

The zig-zag shape of the expandable members 102 can be designed to provide a specific radial stiffness. Such radial stiffness can be important for resisting concentric or eccentric radial forces and maintaining the shape of the stent 100 once deployed.

The stiffness, k, of a ring member 102 when subjected to a hoop load, e.g., as a result of a perfectly concentric lesion, can be approximated by the following relationship:

$$k_{hoop} \propto (Ew^3 t)/(nL^3) \qquad [1]$$

where each expandable ring member 102 include a series of n struts 120 disposed around the circumference of the stent 100, each strut having a length L, a width w, a thickness t, and made of a material having a Young's Modulus E. In this mode of loading, the "hoop" stiffness is dominated by the cube of the strut width, and inversely related to the cube of the strut length.

Moreover, the stiffness, k, of a ring member 102 when subject to a pinching or buckling load, e.g., as a result of eccentric loads, can be described by a different stiffness formulation:

$$k_{pinching} \propto (Ewt^3)/(nL^3) \quad [2]$$

In this mode of loading, "pinching" stiffness is dominated by the cube of wall thickness, rather than strut width as it was for hoop stiffness. An effective stent for treatment of a vessel subject to pinching or buckling, therefore, will maximize wall thickness to maximize resistance to the pinching load experienced.

The zig-zag shape of the expandable members 102, in combination with the radial stiffness, can be further designed to provide a specific restorative force, acting in a radially outward direction to restore the patency of the a constricted lumen. Having a high restorative force can be important for providing the initial expansion force and for resisting concentric or eccentric radial forces placed on the stent 100 after implantation.

Figure 3A:
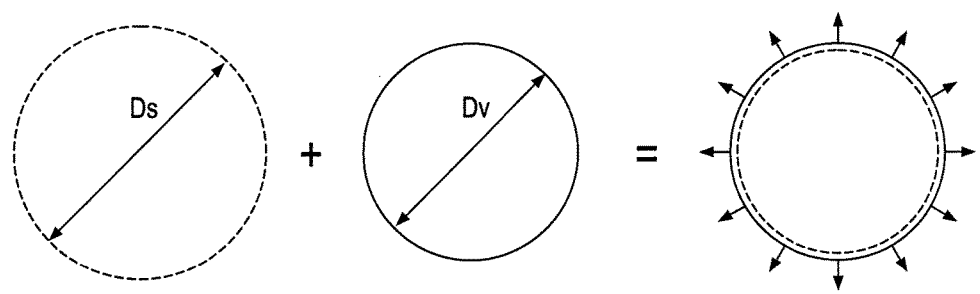
FIGS. 3A-3B are depictions of the relationship of the stent to vessel and lesion diameters.
Figure 3B:
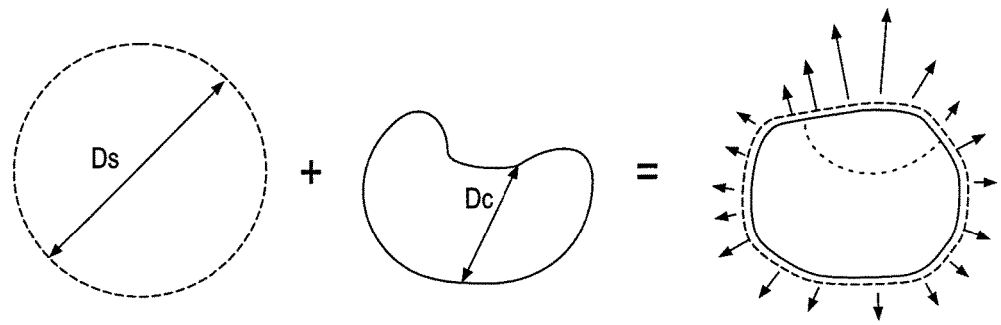

Referring to FIGS. 3A-3B, to increase the force applied, the diameter Ds of each expandable member can be chosen to be somewhat larger than the largest effective diameter Dv of the reference vessel. Referring to FIG. 3A, for areas having concentric lesions, the expandable member can be designed to have a uniform expansion force. As such, Ds−Dv>0, and the inserted expandable member can remain in contact with the vessel at all times and all locations. In contrast, referring to FIG. 3B, for areas having eccentric lesions, such as in areas where compression, luminal webbing, or spurs further constrict the effective lumen diameter to Dc, the expandable member 7 can be designed to provide additional force at a particular location. Accordingly, the inserted expandable member will be more constrained (or "oversized") in this area of constriction than in the area of normal lumen: (Ds−Dc)>(Ds−Dv).

The amount of restorative force generated by a strut deflected by a distance δ can be expressed by the following equation for hoop force:

$$F_{hoop} = [(12*E*I)/(L^3)]*\delta$$

where E is Young's Modulus for the material, I is the moment of inertia of the strut with respect to its axis of bending as the stent expands or contracts, L is the length of the strut, and δ is the magnitude of strut deflection. Thus, the amount of force that a particular module can apply is enhanced by maximizing the number of struts around the circumference Axial Flexibility It is commonly desirable to provide a stent structure that allows for smooth contouring and apposition in curved vessels or lumens following an irregular axial path. In such cases, the ideal stent can vary its local curvature in a continuous manner to accommodate any state of vessel bending. To maximize axial flexibility, it is desirable to decrease the axial length of strut elements 120, as bending is more likely to occur at the transition between the adjacent expandable members 102. Generally, axial flexibility of the stent is improved by minimizing the width w and thickness t of these strut elements 120, as this decreases the overall stiffness of the structure. Similarly, as the number of struts 120 around the circumference increases, strut width typically decreases, as there is a finite amount of material from which to form the struts, which also tends to improve axial flexibility.

Bridging Members

Referring back to FIG. 1, adjacent bridging members 104 can have bridging elements 140 that extend between apices 122 of adjacent expandable members 102. The bridging elements 140 can extend in a circumferential direction, i.e. between 0° and 90° from the longitudinal axis 110 of the stent.

As shown in FIG. 1, the bridging elements 140 of adjacent bridging members 104 along the longitudinal axis 106 of the stent can have an opposite pitch from one another. The bridging members 104 can thus alternate between bridging elements 140a that extend from a first apex 122a to a second apex 122b at a clockwise angle (otherwise known as a negative angle) with respect to the longitudinal axis 110 and bridging elements 140b that extend from a first apex 122c to a second apex 122d at a counter-clockwise angle (otherwise known as a positive angle) with respect to the longitudinal axis 110 of the stent.

The alternating pitch of the circumferential bridge members 104 advantageously prevents the stent 100 from responding with a bias to torsional loading. If all of the bridging elements 104 were alternatively oriented with the same pitch, a torsional load of a given direction may cause the stent to twist and/or to preferentially expand or contract in diameter. With an alternating pitch, the bias to torsional loading can be partially removed. That is, alternating the pitch allows the tendency for one bridging member 104 to rotate clockwise to be balanced by the adjacent bridging member's tendency to rotate counterclockwise. Further, having alternating pitch allows the stent 100 to accommodate significant axial, bending, or torsional deformation with relatively low amounts of strain because the loads can be distributed across the bridging elements 140. In some embodiments, the pitch of adjacent bridging members 104 is exactly opposite so as to fully balance out the torsional load across the stent 100. In other embodiments, a desired amount of twist can be purposefully imparted into a first section of the stent 100 and balanced out in another section of a stent 100. In still other embodiments, the stent can include an overall twist caused by an unbalanced pitch. Imparting an intentional twist into all or a section of the stent 100 might be important for matching a twist in a particular anatomy.

Figure 4:
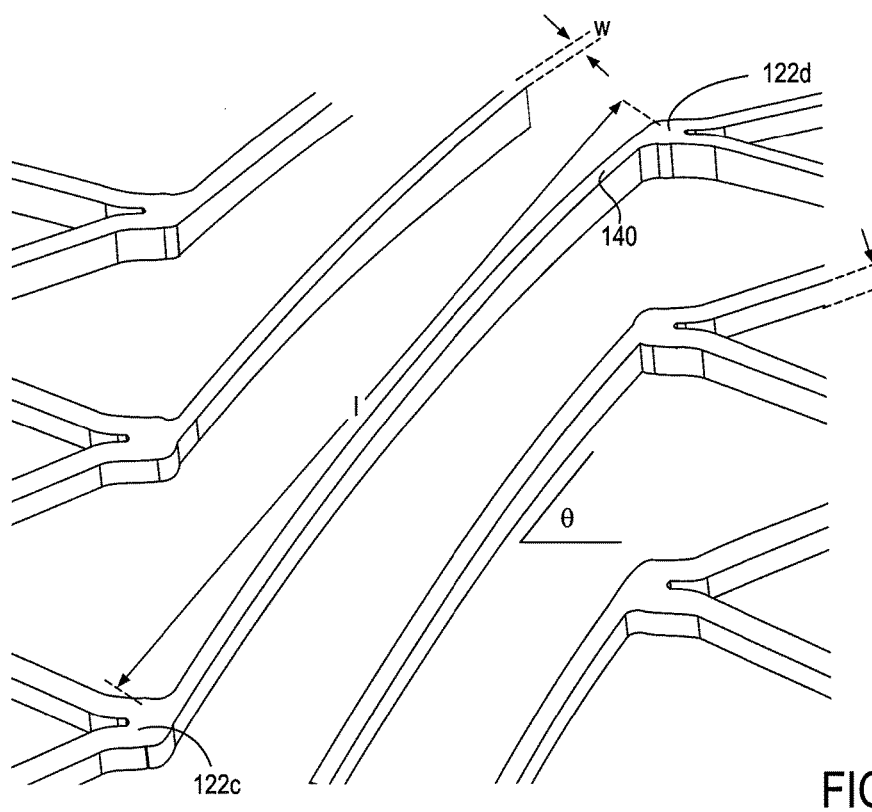
FIG. 4 is a close up of a portion of a bridging member described herein.

Referring to FIG. 4, a bridging element 140 can extend between each pair of internal apices 122c and 122d of expandable members 102. The circumferential bridging element 140 can have a length l as measured from apex 122A to apex 122B. Moreover, the angle between the length of the strut element 601 and a line extending parallel with the longitudinal axis of the strut can be offset by a circumferential angle θ. The angle θ can be used to describe the change in circumferential position traversed by a circumferential bridging element 140.

Flexibility

The bridging members 104 can be used to influence the axial flexibility of the stent 100 when subjected to various loads. Flexibility is particularly important for those portions of the stent that approach or cross a ligament, bone, muscle or other anatomical feature that may alter or influence the response characteristics of the treated vessel.

Figure 5:
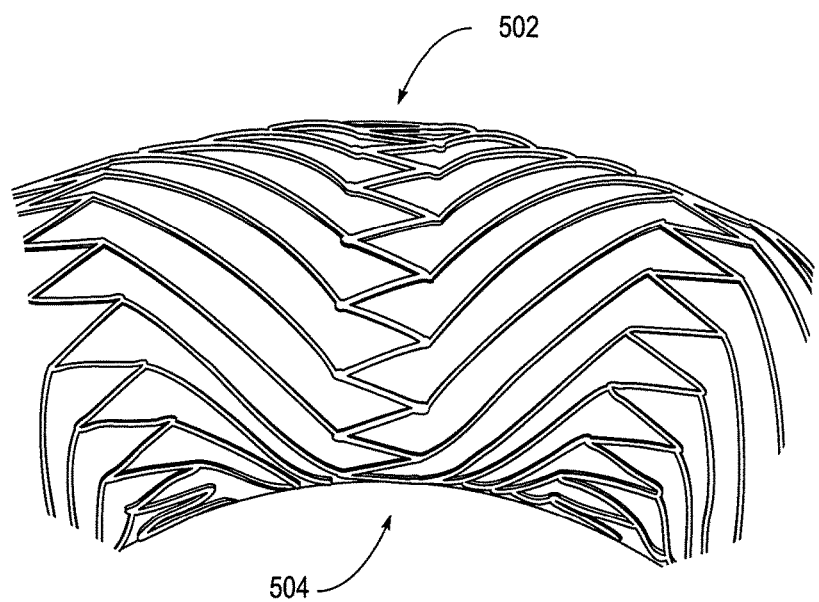
FIG. 5 shows a stent as described herein bent axially.

Referring to FIG. 5, as the stent 100 bends axially, the bridging elements along the outer curve 502 will spread apart, while the bridging elements along the inner curve 504 will draw closer together. Thus, as the length of a bridging element is increased, the longitudinal flexibility of the stent will increase because the bridging elements will be able to spread apart further along the outer curve 540. Likewise, the greater the angle θ, the greater the longitudinal flexibility of the stent because each bridging member 140 has a greater ability to stretch along the outer curve 540. As with the strut elements 120 described above, increasing the width w and thickness t of the bridging elements 140 tends to increase the overall stiffness of the structure, and thus adversely impact axial flexibility of the structure. Again, increasing the number of such elements 140, while correspondingly reducing the width of individual elements, allows for bending loads to be distributed more uniformly throughout the structure, and generally improve axial flexibility.

Radial Stiffness

The bridging elements contribute to radial stiffness by a relation of l*θ. As θ varies from an axial orientation to a circumferential orientation, the contribution to radial stiffness ranges from low to high. Bridging elements that are axially oriented have no impact, as they simply translate in a radial direction as the stent is expanded, contracted, or exposed to hoop forces. Bridging elements that are circumferentially oriented, however, are oriented in the same direction as hoop forces, contribute to carrying hoop loads, and therefore increase hoop stiffness of the structure. The magnitude of this effect is proportional to the length l of the bridging element 140; very short bridging elements have little impact at all, while longer bridging elements have an increasing impact.

Rotating/Foreshortening

Stents commonly experience changes in orientation or length during the transition from constrained to expanded, or the vice versa. For example, a decrease in length can occur between the constrained stent and the expanded stent, called foreshortening. One component of foreshortening results from the change in angle of the struts 120 comprising the expandable members 102 as the strut is expanded.

The bridging members 140 can compensate for some of the foreshortening experienced by the structural elements. As the length l and the angle θ of the bridging elements 140 decrease, the difference in length between the constrained and expanded condition of the stent 100 also decreases. Minimizing the amount of foreshortening is generally desirable to improve the predictability and accuracy of deployment and positioning. Thus, compensating for foreshortening provides motivation to moderate the length l and angle θ of the bridging members 104.

Further, as length l and angle θ decrease, the expandable ring members 102 will have a decreasing tendency to rotate relative to each other as the stent expands or contracts. Relative rotation between expandable ring members 102 can cause the stent to be unstable, disrupt the surrounding tissue, and/or exert undesirable forces or strain on the surrounding structures, providing further motivation to moderate the length and angle θ. Moreover, because the angle θ changes as the stent is expanded or constrained, the relative rotational twisting experienced between adjacent expandable ring members 102 during expansion or constraining also increases.

Examples

Figure 6A:
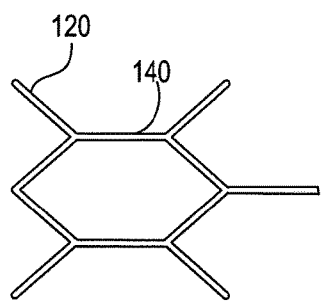
FIG. 6A shows a stent having bridge elements arranged axially.

As an extreme example, consider holding the length l constant and varying the angle θ in a hypothetical series of different designs. In a first design, referring to FIG. 6A, as the angle θ approaches 0°, the bridging elements 140 approach an orientation parallel to the longitudinal axis of the stent. At this extreme, the bridging elements 140 have virtually no contribution to the radial strength of the stent.

As the stent expands or contracts, assuming that the bridging elements 140 maintain their horizontal orientation, there is zero relative rotation between adjacent expandable ring members. Further, these horizontally oriented bridging elements inhibit bending flexibility.

Figure 6B:
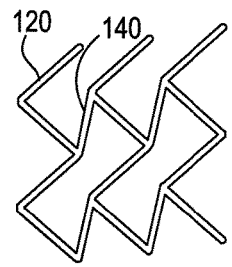
FIG. 6B shows a stent having bridge elements arranged circumferentially.

In a second design, referring to FIG. 6B, as the angle θ approaches 90°, the bridging elements 601 approach a circumferential orientation. At this extreme, the bridging elements 601 have a significant contribution to the radial strength of the stent. Moreover, as the stent expands or contracts, the relative rotation between expandable ring members can be significant (it increases with increasing bridging element length). And at this extreme, the circumferentially oriented bridging elements 140 promote bending flexibility.

Stent Characteristics as a Whole

The stent 100 can be formed from a superelastic material. In one specific aspect, the superelastic material is Nitinol, an intermetallic compound having approximately 50.8 atomic percent Nickel and the balance Titanium. Nitinol has the unique properties of shape memory and superelasticity, and in this application is designed to take advantage of the material's ability to withstand unusually high levels of strain (up to 8% or more), without experiencing plastic deformation. The material can have an unusually pronounced hysteresis effect in its stress-strain relationship: when subjected to loading, stresses are relatively high, as they reach the upper plateau (UP) where a phase change from austenite to martensite occurs. When the material is unloaded, stresses are relatively low, as seen in the lower plateau (LP) where the material transforms from martensite to austenite. The magnitude of the difference between UP and LP stresses is determined by material composition, as well as thermal and processing history. In some embodiments, the transition temperature for the material, known as the Austenite Finish (Af) temperature is preferably set between 10 degrees and 37 degrees C. Preferentially, the Af temperature is set close to body temperature to maximize the hysteresis effect of the material, increasing the difference between UP and LP. As such, forces exerted by the stent as it unloads (expands) from its constrained state are minimized. This force, described as Chronic Outward Force (COF), is controlled by the LP stress. Conversely, the forces exerted by the stent when it is loaded (subjected to external compression) are maximized. This force, described as Radial Resistive Force (RRF), is controlled by the UP stress.

When all internal apices 122 of a stent are connected together through a bridging element 140, as shown in FIG. 1, the stent can be termed a "closed cell" strut. Advantageously, by having a "closed cell" as opposed to an "open cell" stent can prevent webbing or spurs of a lesion from prolapsing through the struts to compromise the lumen. Conversely, if a stent is "open cell," in which some internal apices are unconnected, the stent can move more freely for enhanced flexibility. In some embodiments, the modules of the stents described herein can be modified such that a closed cell architecture is provided in some stent regions and an open cell architecture is provided in other regions. For example, the areas of the stent expected to lie within the regions of localized constriction can have a closed cell architecture while other areas have an open structure.

Stents are typically placed within a lumen to restore patency of a compromised lumen, resolve obstructions caused by disease or anatomical formations, and thereby improve flow. Obstructions within the lumen are often irregular or non-uniform in nature, and consequently it is desirable for the stent to provide uniform support throughout its contact area with the vessel, and minimize the area of any unsupported regions. "Scaffolding performance" is a term used to describe the ability of a stent to serve this purpose. Cell size, the area bounded by a closed region of struts or bridges, is one measure of scaffolding performance. Minimum inscribed circle (MIC), the smallest circle (or more properly, sphere) that can fit through the structural elements of the stent, passing from inside its cylindrical form to outside, is another measure. Both cell size and MIC can vary as the stent is expanded, stretched, twisted, or otherwise deformed. Ideally, both are minimized throughout any expected loading conditions experienced by the stent. Scaffolding performance tends to improve with the number of elements around the circumference and along the length; more elements of a smaller size will provide more uniform coverage and support for small and irregular obstructions that the stent may oppose in the lumen.

Typically, designs that provide excellent scaffolding characteristics and outward support are also relatively axially stiff, and therefore experience high local strains with localized axial displacement, bend, or torsional loads. Conversely, designs that offer excellent axial and bend flexibility typically suffer from poor local scaffolding performance as local regions of the stent may flex apart to accommodate a bend, this same local flexion typically exposes a gap in scaffolding support, often at the very region where it is most needed. The stents described herein addresses each of the concerns to provide a superior platform for treatment of various anatomical areas of the body.

Advantageously, the properties of the stents described herein can be customized along the length of the device to correspond to the physiology that is common with a particular anatomy or condition. Thus, each stent can have multiple sections, each section including modules that are modified to have a particular property.

FIG. 6C shows a chart of the effect of several variables on the flexibility, stiffness, rotation, and scaffolding, where + indicates positive correlation, ++ indicates strong positive correlation, − indicates negative correlation, −− indicated a strong negative correlation, and 0 indicates no influence. Thus, for example, to make a section more axially flexible, the bridge members can include a greater number of bridge elements circumferentially or have elements with a longer length, a higher pitch, a lower width, or a lower thickness. Likewise, expandable members can have a higher number of struts circumferentially, or have struts elements with a longer length, lower width, or lower thickness. To make a section more radially stiff, there can be fewer strut elements in the expandable ring member, or each strut element can have a shorter length, a higher width, or a higher thickness. Likewise, the bridging members can have a lower number of bridging elements circumferentially, or each bridging element can have a higher length, a higher pitch, a higher width, or a higher thickness. To make a section less rotatable, the bridging elements can have a shorter length or a lower pitch. Scaffolding performance is improved by increasing the number of elements around the circumference, and along the length, and minimizing the freedom of these elements to move apart from each other as the stent is expanded, placed in a bend, or otherwise deformed. These parameters can be adjusted and balanced so as to optimize the performance of the stent for a given indication.

IVCS Stents

Chronic venous insufficiency (CVI) is a disease in which the function of the venous system is compromised. As a result of CVI, blood tends to pool in the lower extremities, and insufficient blood may be returned to the heart for re-oxygenation. The patho-physiology of CVI commonly involves veins of the lower extremities and/or pelvic area: the femoral veins, iliac veins, and inferior vena cava. CVI is associated with deep vein thrombosis (DVT), a condition resulting from clotting of stagnant blood in the deep vein system. CVI is also associated with varicose veins in the superficial venous system, a condition relating to incompetent venous valves. CVI is a progressive condition that can result in leg pain and swelling, edema, and ulcers of the leg or ankle.

Figure 7A:
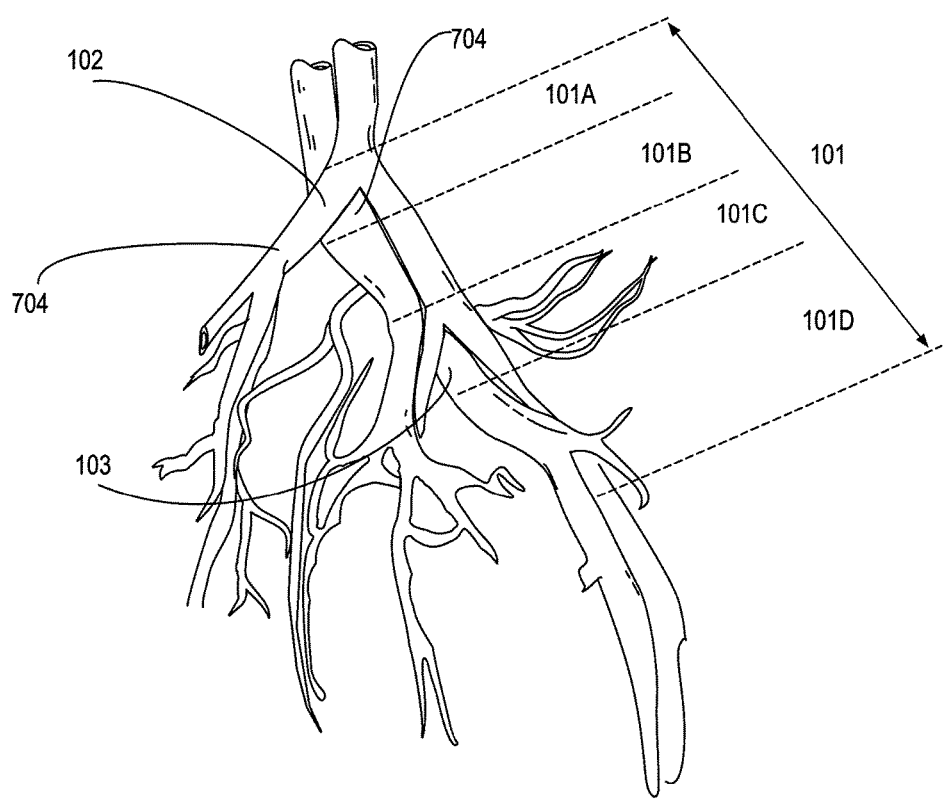
FIG. 7A is an illustration of the anatomy of the venous system within the pelvic region.
Figure 7B:
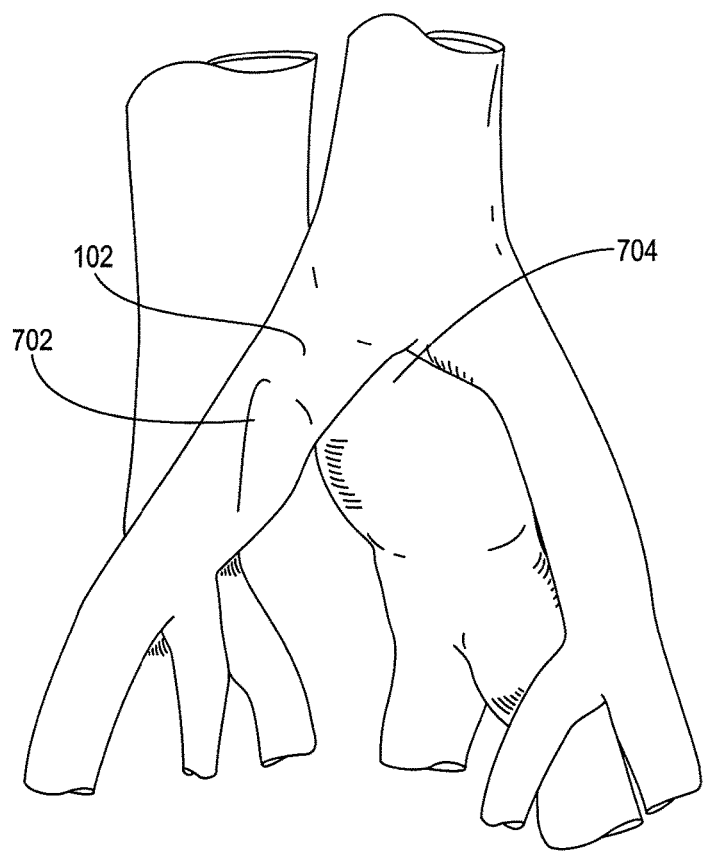
FIG. 7B is an illustration showing the spatial relationship of the anatomy of the right common iliac artery and the left common iliac vein whereby portions of the left common iliac vein are pinched by the right common iliac artery.
Figure 7C:
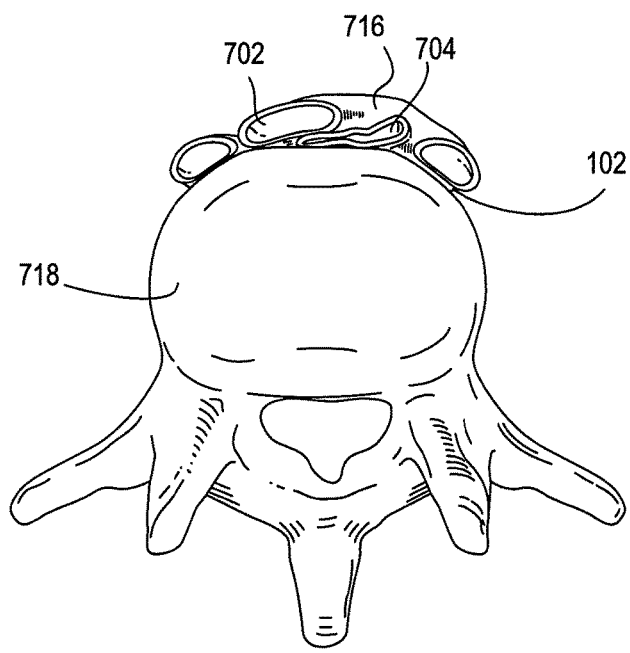
FIG. 7C is an illustration demonstrating the compression of the left common iliac vein between the spine and the right common iliac artery.

A condition known as iliac vein compression syndrome (IVCS), also known as May-Thurner syndrome, or pelvic spur syndrome is recognized as a cause of venous thrombo-occlusive disease. Referring to FIG. 7A, IVCS is commonly observed at the confluence of the common iliac veins, where the right iliac artery 702 crosses the left common iliac vein (LCIV) 704. As shown in FIGS. 7B and 7C, the IVCS can cause compression of the LCIV 704 between the artery 716 and the spine 718. Symptomatic chronic nonmalignant obstructive lesions most commonly occur in region 101 between the confluence of the iliac veins to the inguinal ligament. Further, compression and consequent webbing or spurs are most common at region 101A where the right iliac artery 702 crosses the left common iliac vein. A similar anatomical condition can occur at region 101C where the left internal iliac artery crosses the external iliac vein. In these regions, chronic pulsatile compression is believed to cause the formation of intraluminal venous webs or spurs. These anomalies have been described as chronic nonmalignant obstructive lesions.

Such obstructive lesions may be observed in clinical practice by diagnostic procedures including venography or intravascular ultrasound. It is believed that these lesions are an important contributor to the cascade of events leading to CVI of escalating severity. These lesions may be dilated by balloon venoplasty in an attempt to restore venous flow, but this technique has been found to provide inadequate resolution in many cases. Studies have found that treating these lesions with intravenous stents is a safe and effective therapy that is more durable than balloon venoplasty alone. To date, no stent has been designed specifically to treat obstructive lesions of the pelvic veins. Therefore, stents to help treat the particular issues related to obstructive lesions of the pelvic veins are needed.

Figure 8:
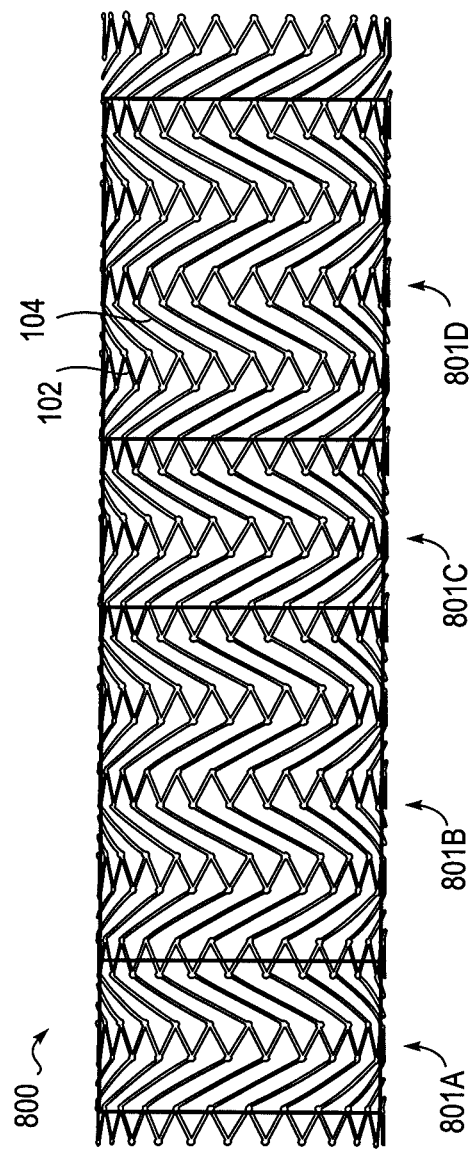
FIG. 8 shows an exemplary stent for treatment of IVCS.

Referring to FIG. 8, a stent 800 for treatment of IVCS may be preferentially designed by varying the parameters described herein. The stent 800 can have a length that covers the region 101, e.g., be at least 130 mm in length. The expanded diameter of the stent 800 can be between 120 nm and 20 mm, such as approximately 14 mm.

The stent 800 can include several expandable members 102 connected by bridging modules 104. The stent can include sections 801A, 801B, 801C, and 801D that are configured to line up with regions 101A, 101B, 101C, and 101D, respectively, of the artery.

Section 801A can be configured to maximize stiffness or resistance to compressive force in the region of the right iliac artery compression 101A. Likewise, section 801C can be configured to maximize stiffness or resistance to compressive force in the region of the left internal artery compressions 101C. Thus, for example, the strut length of the strut elements in the ring members 102 can be decreased and/or the strut thickness can be increased in sections 801A and 801C relative to section 801B so as to maximize stiffness in those areas. For example, there can be 30 to 60 struts, such as 48 struts in each ring member 102 of sections 801A and 801C. Further, the length of the struts in each ring member 102 of sections 801A, 801C can be between 1 and 4 mm, such as approximately 2.1 mm. The width of the struts in each ring member 102 of sections 801A and 801C can be between 0.1 mm and 0.3 mm, such as approximately 0.15 mm. The thickness of the struts in each ring member 102 of sections 801A, 801C can be between 0.1 mm and 0.5 mm, such as between 0.2 mm and 0.4 mm, such as approximately 0.36 mm. Moreover, the length of the bridging elements 140 of bridging members 104 in sections 801A and 801C can be increased and/or the angle θ can be increased relative to bridging members 104 in section 801B.

Further, section 801D can be configured to maximize flexibility in the region where the LCIV approaches or crosses the inguinal ligament (region 101D). In one embodiment, the total expanded circumference of the stent is 14 mm*π=44 mm, and the length of the bridging elements of the bridging modules 104 of section 801D is approximately 4.4 mm. The angle θ, therefore, is approximately 10% of the circumference, or 36°, when the stent is in its expanded configuration. In the constrained condition, the circumference of this stent is 3.2 mm*π=10 mm, so the constrained θ of bridging modules 104 in section 801D is 44% of the circumference, or 160°. As this stent is expanded or constrained, adjacent expandable ring segments in section 801D undergo rotation of the difference in the expanded and contracted θ, 160° minus 36°, or 124°. Further, the struts of the ring members 102 can be configured to have a length of approximately 1-4 mm. These design parameters are chosen so as to enhance flexibility without compromising scaffolding performance.

Femoral Artery Stents

Arterial disease occurs when the natural lumen of an artery narrows or closes, such as when fibro-fatty deposits or calcified plaques grow within the layers of the artery and spread throughout the arterial system. Consequences of coronary arterial disease may range from angina to myocardial infarction and sudden death.

Figure 9C:
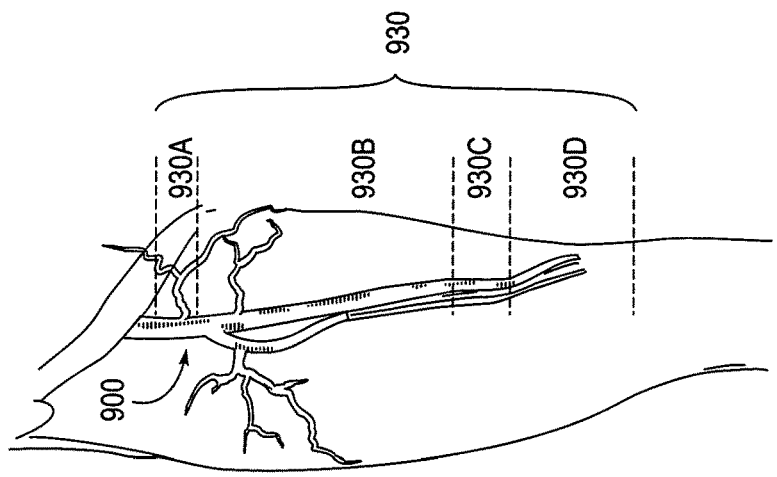
FIGS. 9A-9C show the femoral arteries and surrounding anatomy.
Figure 9B:
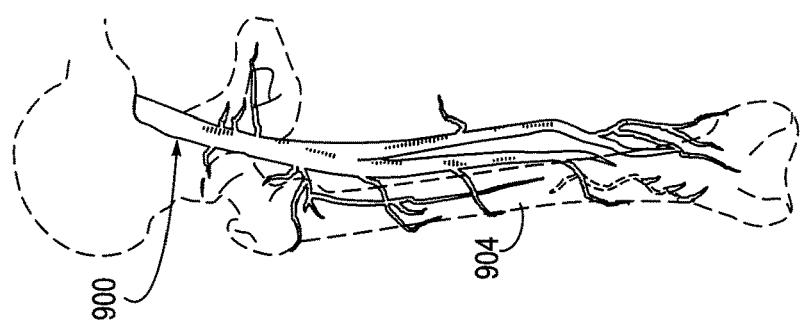
Figure 9A:
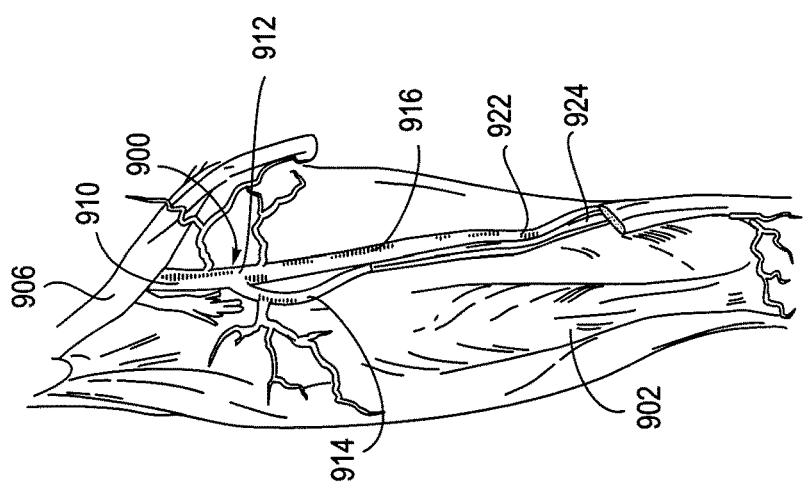

The superficial femoral artery (SFA) is commonly affected by peripheral arterial disease that may be associated with symptoms ranging from mild claudication and difficulty walking to chronic limb ischemia and partial amputation. FIGS. 9A-9C show the femoral arteries 900 in relation to surrounding muscles 902 and skeletal landmarks 904. As the external iliac artery passes posterior to the inguinal ligament 906, its name changes to the common femoral artery 910, which branches (at 912) into the profunda 914 and the superficial femoral artery 916. The profunda 914 supplies blood to the thigh and the superficial femoral artery 916 carries blood to the lower limb.

The SFA is unique in the human arterial system, as it traverses the thigh region with few branches, serving to deliver oxygenated blood to the lower limb by way of the popliteal and tibial arteries. Transiting from the region of the hip to the knee, the SFA passes through several muscle groups, and is subjected to one of most dynamic and mobile environments in the human anatomy. While disease in the SFA can be localized, it is frequently diffuse, commonly spanning 10 cm or more.

The superficial femoral artery is effectively pinned in two major locations: in area 930A near its origin in the area of the inguinal ligament 910 and the branch 912, and in area 930C near its terminus in the area of first genicular arteries 922 and the Hunters canal 924. Between these points, in region 930B, the vessel can be quite mobile, limited to some extent by minor branch vessels, often to a greater extent by rigid calcifications within the diseased regions of the vessel. The areas of the vessel that are less constrained—for example, the area 930B between the inguinal ligament and hunters canal and the area 930D, and away from areas of localized calcification—may be subjected to highly localized deformations including twisting, stretching, and/or compression with flexion of the limb.

The dynamic challenges of this disease prone area of the SFA create a severe fatigue environment for metallic implants intended to improve lumen diameter and distal perfusion. Stents placed in this region have commonly been found to fracture, raising concern about such implants failing to perform their function, creating injury, or causing additional risks to the patient. Accordingly, a stent that is capable of withstanding such an environment is needed.

Figure 10:
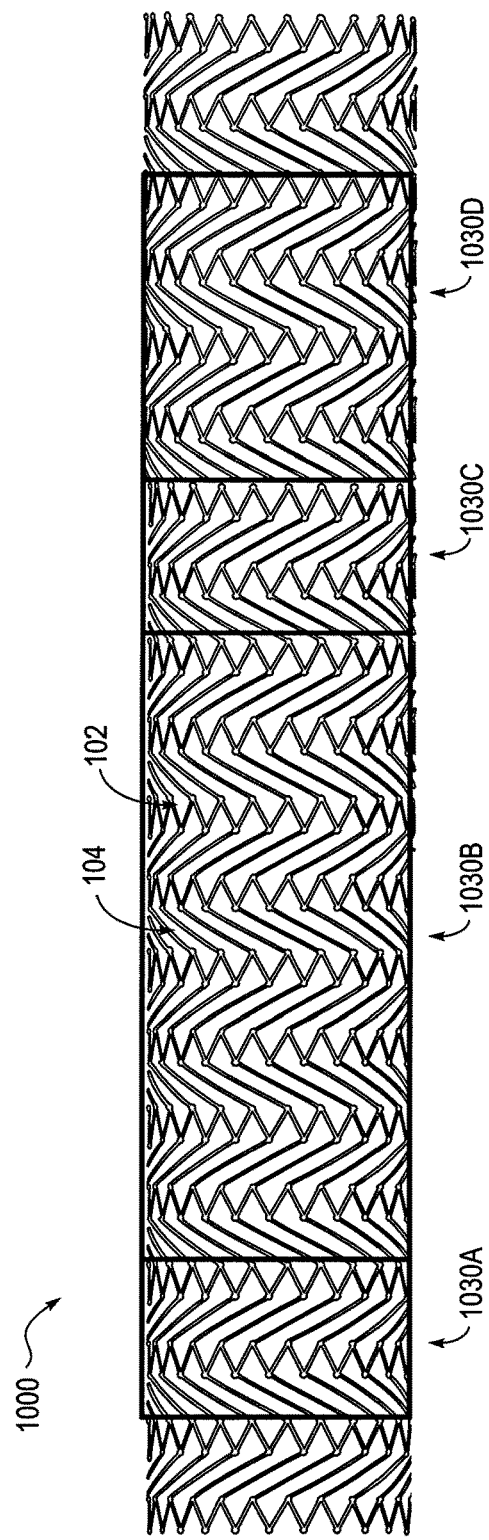
FIG. 10 shows an exemplary stent for a femoral artery.

Referring to FIG. 10, a stent 1000 for treatment of the femoral arteries includes alternating circumferential bridging members 104 and expandable ring members 102. The stent can include sections 1030A, 1030B, 1030C, and 1030D that are configured to line up with regions 930A, 930B, 930C, and 930D, respectively, of the artery. Thus, the stent 1000 can have an expanded diameter of slightly more than the diameter of the femoral artery to provide sufficient outward force. For example, the stent 1000 can have an expanded diameter of greater than 7 mm, such as approximately 8 mm.

The sections 1030A and 1030C intended to be placed in the pinned area of the adductor hiatus and canal can be configured to be of higher strength or stiffness relative to sections 1030B and 1030D. For example, the wall thickness can be increased relative to sections 1030B and 1030D and/or the ratio between the wall thickness and the strut width can be increased relative to sections 1030B and 1030D. Furthermore, to increase the hoop stiffness in this area, the length and angle of the bridging elements may be increased. Furthermore, to increase the hoop stiffness in this area, the length and angle of the bridging elements may be increased.

Further, section 1030B of the stent 1000 that is intended to be placed in the highly mobile region 930B between the profunda 804 and the adductor hiatus 805 and in the mobile region 930D can be configured to be more flexible relative to sections 1030A, 1030C. For example, the alternating circumferential bridging members can be designed to allow increased flexibility by increasing the length and angle θ of bridging elements in the bridging members 104 relative to sections 1030A and 1030C.

Coronary Artery Stents

Figure 11:
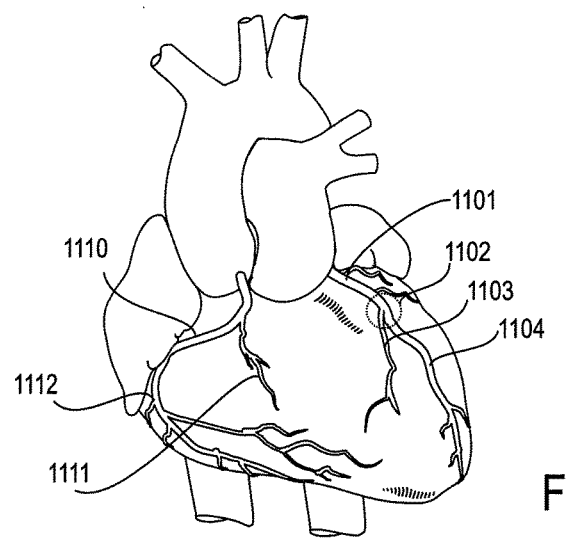
FIG. 11 shows the coronary arteries.

Coronary arterial disease is among the most important areas of interventional medicine. Traditional stenoses of the coronary arteries have been treated with balloon expandable stents because of their high strength, ease of use, and versatility. Referring to FIG. 11, the modular stent described herein could be useful in the coronary arteries 1100 for bifurcation 1102 of the left main (LM) artery 1101 to the left anterior descending (LAD) artery 1104, the left main artery to the circumflex (CX) artery 1103, or are in the region of side branches between right coronary artery (RCA) 1110, LAD 1104, or CX 1103 and corresponding diagonal branches along their length. Similarly, self expanding stents could be used for stenting the LM 1101 itself, and potentially the ostium 1115 of the LM 1101 and RCA 1110 at the location of the aortic root 1114. Particularly in these areas, it is critical that the stent accommodate significant variation in shape in-situ, i.e., the final contour of the implanted stent may need to be significantly non-cylindrical and include abrupt changes in local diameter or cross section.

Figure 12A:
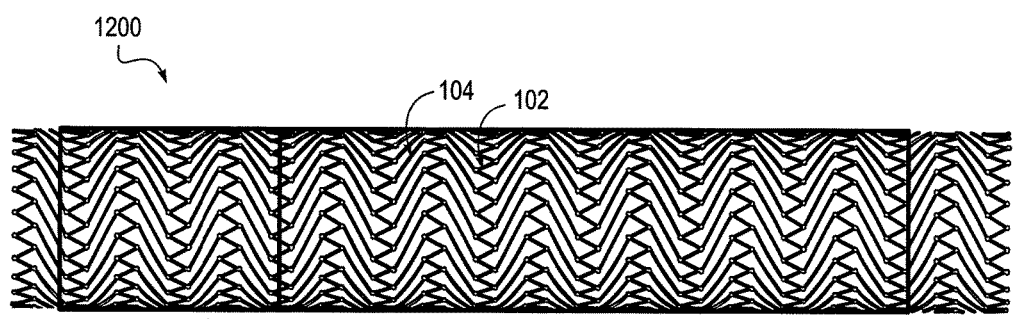
FIGS. 12A-12B show an exemplary stent for a coronary artery.
Figure 12B:
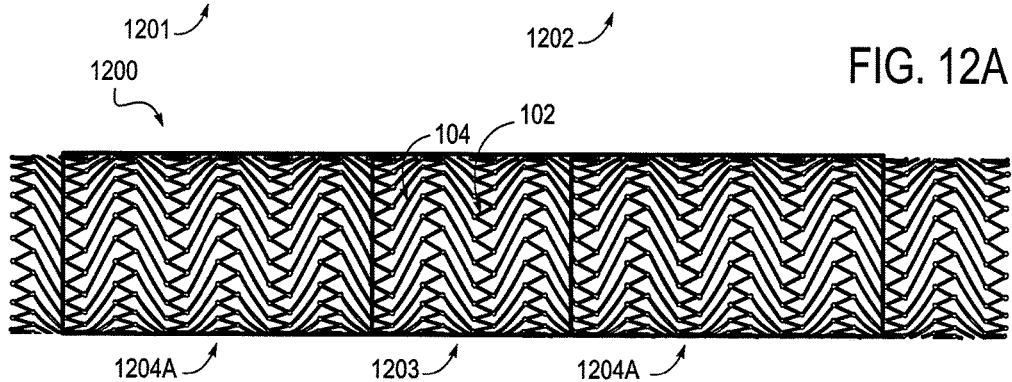

Referring to FIGS. 12A-12B, a stent 1200 for treatment of coronary artery disease includes alternating circumferential bridging members 104 and expandable ring members 102. The stent 1200 is configured to abruptly change one or more of its shape, contour, local diameter, or cross sectional profile to accommodate for the changes of the coronary arteries. In one embodiment, shown in FIG. 12A, the stent 1200 includes a section 1201 and a section 1202. Section 1201 can be configured to be positioned near an ostium or the origin of a branch vessel. Accordingly, section 1201 can be more flexible than section 1202. Thus, for example, the bridging elements of the bridging members 104 can be longer in section 1201 than in section 1202. Further, the pitch of the bridge members 104 can be increased relative to section 1202. Additionally, section 1202 can be configured to provide more uniform vessel support than section 1201 and/or can be configured to provide drug delivery to the remainder of the stented coronary artery. The shorter bridging elements and small pitch relative to section 1201 can provide increased support in section 1202.

In another embodiment, shown in FIG. 12B, the coronary artery stent 1200 includes a section 1203 between adjacent sections 1204A and 1204B. Section 1203 can be configured to be located at the site of a branch vessel, while sections 1204A and 1204B can be configured to be proximal and distal to the branch location. Accordingly, section 1203 can be configured to be more flexible than sections 1204A and 1204B. Thus, bridging elements of the bridging members 104 in region 1203 can be longer and/or have a higher pitch than the bridging elements in regions 1204A and 1204B.

Renal Artery Stents

Figure 13:
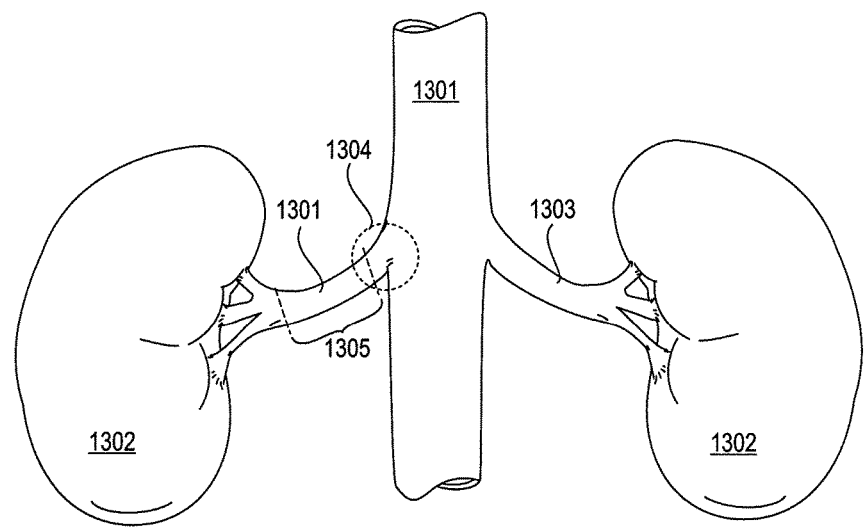
FIG. 13 shows the renal arteries.

Referring to FIG. 13, the rental arteries are prone to arterial disease, particularly in the ostium 1304. However, stenting can be difficult because the renal arteries 1303 are relatively mobile during the respiratory cycle. The kidney 1102 can move several millimeters during the respiratory cycle, while the aorta 1101 moves separately. The renal arteries 1303, joining the kidneys to the aorta, may therefore experience significant bending, angulation, or displacement between inhalation and expiration. Traditional inflexible stents may adversely impact the normal anatomy in this region, while flexible stents may experience large cyclic deformations and strains, potentially resulting in fracture. It is therefore important to provide a renal artery stent that can be sufficiently flexible, can accommodate the complex shape of the renal ostium, and can provide substantial radial stiffness for the body of the renal artery.

Figure 14:
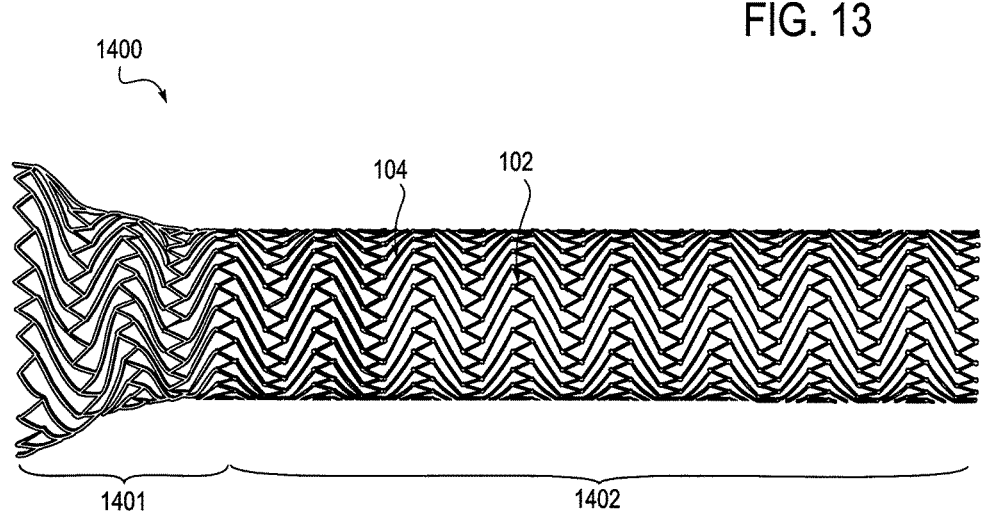
FIG. 14 shows an exemplary stent for a renal artery.

Referring to FIG. 14, a renal artery stent 1400 includes alternating circumferential bridging members 104 and expandable ring members 102. The stent includes a section 1401 configured to be placed at the ostial end of the rental artery and a section 1402 configured to be placed along the rest of the artery. Thus, section 1401 can be more flexible than section 1402 to accommodate for the shape of the ostium. Conversely, section 1402 can be configured to provide higher strength or stiffness than section 1401 to adequately support the rest of the artery. Thus, for example, section 1401 can include longer bridging elements than section 1402, allowing for significant flaring of section 1401 to adequately cover the ostium 1304. Further, section 1402 can include feature shorter and stiffer struts than section 1401.

Carotid Artery Stents

Figure 15:
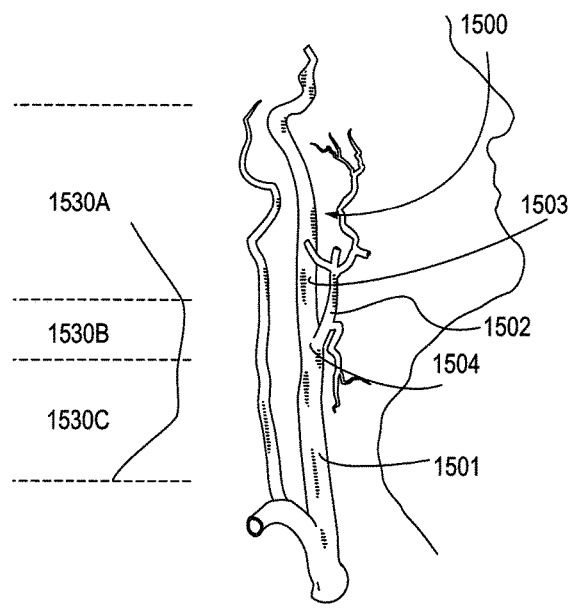
FIG. 15 shows the carotid arteries.

Referring to FIG. 15, the carotid arteries 1500 include the common carotid artery 1501, the internal carotid artery 1503, and the external carotid arteries 1502. The common carotid artery 1201 splits into the internal carotid artery 1503 which delivers flow to the brain, and external carotid arteries 1502 that deliver flow to the other areas of the head and face. The bifurcation 1504, where the common branches into the internal and external carotid arteries, is also described as the carotid bulb or carotid sinus. Carotid arterial disease commonly involves substantial plaque deposits and flow limiting narrowing in the common, and branch carotid vessels, and therefore commonly involves the sinus region. There are several important structures in the region 1530B of the carotid sinus including the baroreceptors in the adventitial layer of the carotid sinus. These baroreceptors are mechanoreceptors modulate the activity of the sympathetic and parasympathetic nervous systems on the basis of pressure and/or stresses in the vessel wall. Angioplasty and stenting in this region can create hemodynamic instability, with detrimental effects on baroreflex, and consequent hypotension or hypertension. Conventional stents, with uniform outward force along the length of the structure, may exacerbate this effect. Accordingly, a stent is needed with enough support so support a lesion in the carotid artery, but enough flexibility to avoid hemodynamic instability.

Figure 16:
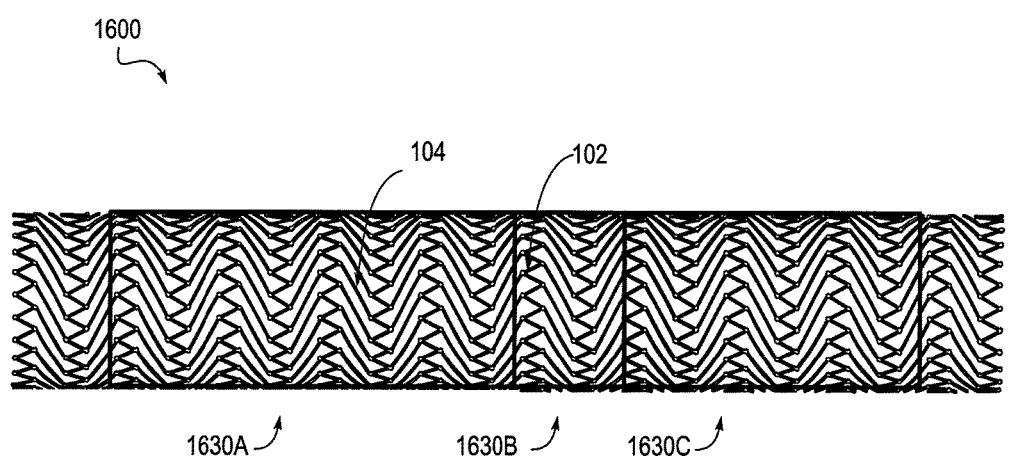
FIG. 16 shows an exemplary stent for a carotid artery.

Referring to FIG. 16, a carotid artery stent 1600 includes alternating circumferential bridging members 104 and expandable ring members 102. The stent includes sections 1630A, 1630B, and 1630C, which correspond to regions 1530A, 1530B, and 1530C, respectively, of the carotid artery. Region 1630B can be designed to allow for the abrupt change in diameter and shape in region 1530B while minimizing disruption of the carotid sinus. For example, the radial stiffness of section 1630B can be reduced and/or the flexibility of section 1630B can be increased relative to neighboring sections 1630A and 1630C.

Fistula Stents

Figure 17A:
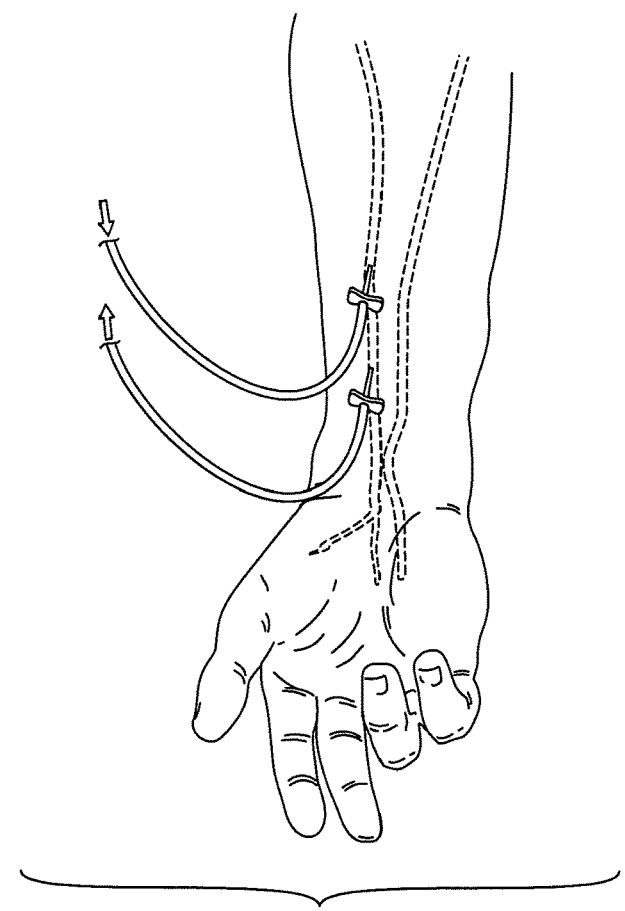
FIGS. 17A-B show hemodialysis access grafts and fistulae.
Figure 17B:
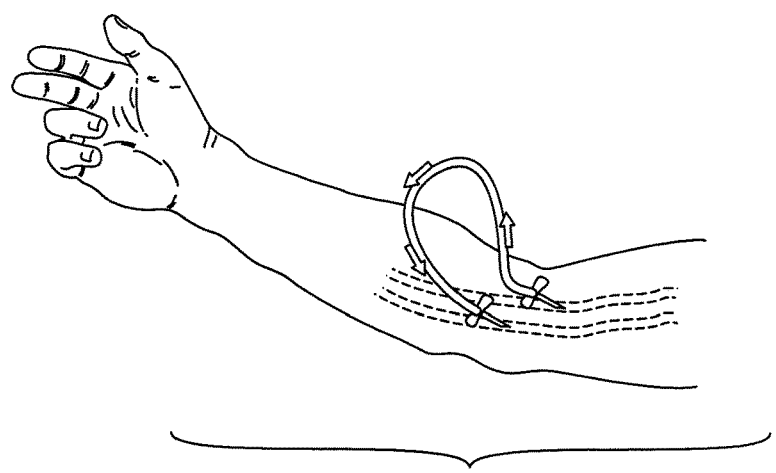

Referring to FIGS. 17A and 17B, the stent described herein could be used at the junction of hemodialysis fistulae 1301 or grafts 1302. In these applications, a stent may need to be placed at the junction of an artery, vein, and/or synthetic graft, and therefore assume an abrupt angle. Furthermore, the stent may have to accommodate a significant diameter change at the site where the fistula or graft joins the native artery, making the modular stent described herein advantageous over traditional stents.

Tracheal Stents

Figure 18A:
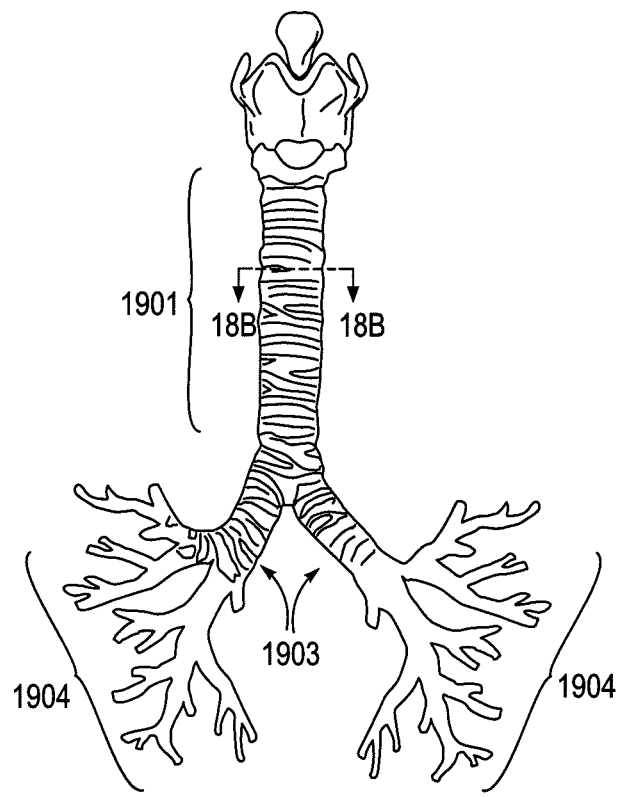
FIGS. 18A-18B show the trachea and bronchi.
Figure 18B:
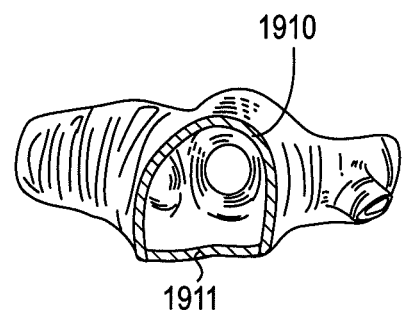
Figure 19A:
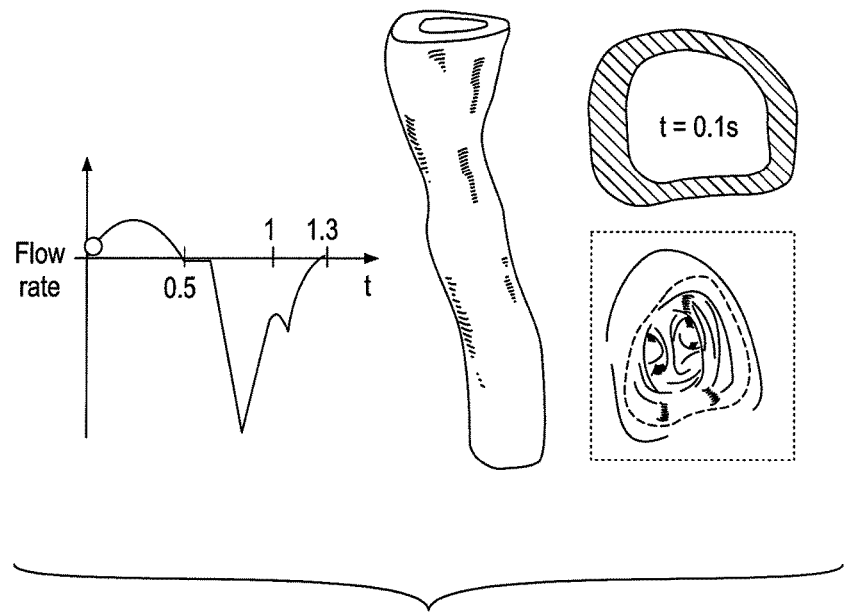
FIGS. 19A-19B show the response of the trachea during coughing.
Figure 19B:
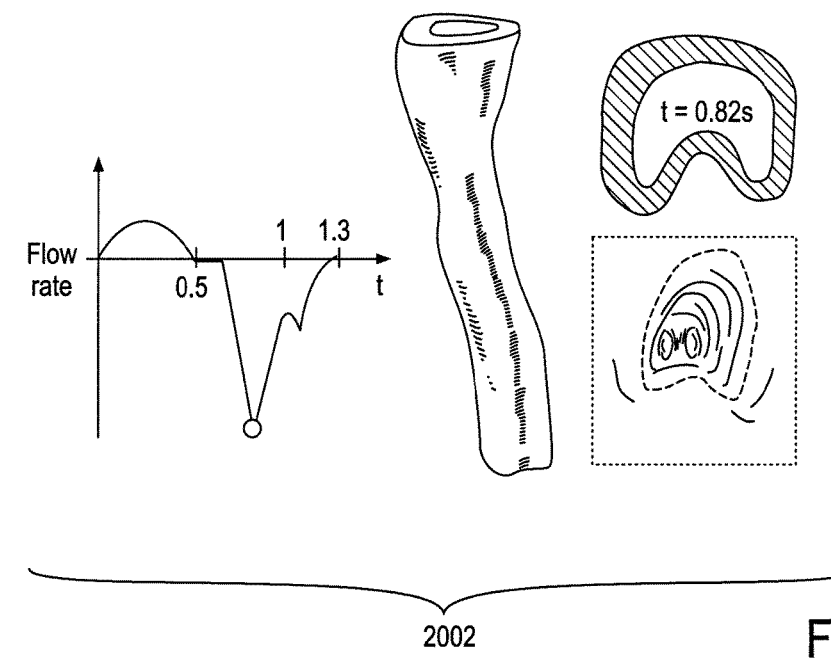

Referring to FIGS. 18A-18B, the trachea 1901 branches into the right and left main stem bronchi 1903, which further branch into lobar bronchi 1904 to feed the lungs. The main stem and lobar bronchi are circumferentially supported by irregular plates of hyaline cartilage. In the main stem, lobar bronchi and below, the cartilage 1910 is partially circumferential, taking the shape of the letter "C," with a fibrous membrane 1911 between the ends of the "C." When foreign matter, phlegm, or other debris becomes lorded in the bronchi or trachea, a cough reflex is triggered. The response of the human trachea during a cough is illustrated in FIGS. 19A-19B. When a cough occurs, the soft tissue in this region allows the substantially circular cross section of the trachea 2001 to collapse into a narrowed crescent shaped channel 2002. The reduced cross sectional area increases the velocity of the air exiting the lungs through this space, helping to propel material out of the trachea. The airways may become obstructed in the case of tumor growth in the region of the lungs or surrounding structures, causing compression of infiltration of the bronchi or trachea.

Stents can be placed in the trachea as a palliative or restorative therapy. Such a stent may provide outward forces to expand the lumen of the airways, prevent compression and/or ingrowth of the tumor, and/or deliver chemotherapeutic or other agents locally. Stents commonly used in this indication have several shortcomings. For example: silicone or polymer based stents have low outward force and can migrate or be expectorated; other stents designed primarily for cardiovascular use have been deployed with limited success, as these devices lack sufficient radial stiffness, thus allowing undesirable compression. Importantly, conventional stents are typically designed to have uniform radial outward forces along the length of the stent, which creates an incompatibility with the normal physiological and/or biomechanical movement of the airway. Furthermore, conventional stents may interrupt or degrade the normal mucociliary transport system of the bronchi and trachea with struts or coverings that are oriented in such a way as to inhibit the normal flow of mucus. Accordingly, a stent is needed that addresses some or all of these limitations.

Accordingly, a modular stent as described herein could be used in the trachea. The circumferential bridging elements could accommodate the need for the airways to transform between a substantially circular cross section to a substantially crescent shaped cross section during a cough. For example, an array of struts axially aligned in a circumferential band ranging up to 180 degrees of the circumference, and oriented toward the dorsal aspect of the airway, can be designed to be more flexible than the struts in an axial band oriented toward the ventral aspect of the airway. The normal configuration of the mucosal epithelium is spiral in nature. Further, the smooth muscle surrounding the airways tissue is arranged in a helical orientation. The epithelium and cilia follow the orientation of the innermost smooth muscle layer. In a preferred embodiment of the present invention, the circumferential bridge elements are oriented in such a way as to be consistent with this orientation. As such, an embodiment for this indication may favor circumferential bridges that are all oriented in the same direction, rather than alternating in direction along the length. Furthermore, the bridges are preferentially oriented in a direction that is closer to axial than circumferential, thus promoting functional mucociliary transport.

Methods of Use

In operation, the stents described herein can be placed in the anatomy of interest. In some embodiments, the physician can first inject a radiopaque contrast medium into the vessel of interest to visualize the path and caliber of the subject veins. Alternatively, or in addition, the physician may introduce an intravascular ultrasound (IVUS) catheter into the vessel of interest to study the cross section of the lumen at all points along its length. The IVUS catheter can be specifically designed to work in conjunction with the stent and delivery system described herein. Preferentially, the IVUS probe would be contained within the profile of a standard 0.035" guidewire, and could therefore be used to replace the conventional guidewire for balloon and stent delivery while providing opportunity for imaging throughout the procedure.

Using the radiopaque markers and/or IVUS guidance, the physician can place a high pressure balloon at the site of the constriction and inflate to a pressure sufficient to dilate the narrowed area. This procedure may be repeated multiple times and at multiple locations to achieve a satisfactory result.

The stent can be constrained within a flexible sheath, preferably such that the sheath is compatible with an introducer sheath having a profile of 10 French or less. In some embodiments, the stent is constrained within this sheath at the time of manufacturing and packaging. Alternatively, the stent can be constrained within a capsule that is packaged separately from the delivery sheath, and coupled with the delivery device before insertion into the patient.

The physician can place a guidewire, such as a 0.035" guidewire, across the site of the target vessel. The delivery system can then be advanced over the guidewire to the target site. The stent can be positioned in the desired location using X-Ray and/or ultrasound guidance.

An actuation mechanism at the proximal end of the delivery system can then be used to retract the outer constraining sheath and allow the stent to expand to its memory diameter. Preferably, the stent will be held fixed relative to the vessel by means of an inner member that engages the stent and is held axially fixed during sheath retraction. The constraining sheath may be designed to retract in a "tip to hub" direction, thereby first expanding and anchoring the end of the stent farthest from the operator. Alternatively, the constraining sheath may be designed to retract from "hub to tip" direction, thereby first expanding and anchoring the end of the stent closest to the operator first. Because placement at the confluence is critical, the direction of approach determines the preferred direction of unsheathing. With the typical antegrade approach, the hub end of the delivery system is near the femoral vein, the tip end is near the confluence, and the preferred direction of deployment is therefore tip to hub. For a more unusual jugular or contralateral approach, the tip end of the stent would be near the femoral vein, the hub end near the confluence, and the preferred direction of deployment would therefore be hub to tip.

After the stent has initially expanded and anchored, it may be advantageous to confirm accurate placement with ultrasound or X-Ray guidance. Further, the stent may contain markers to aid the physician to locate the proximal and distal ends of the stent, as well as any unique features along the length of the stent, or around its circumference. This can be particularly important to denote the location of stent regions with modulated stiffness or flexibility as described above. Radiopacity enhancing features may include coatings, tabs, rivets, inserts, or other features composed of metals including tantalum, platinum, gold, palladium, silver, or combinations thereof. Alternatively or in addition, it may also be advantageous to similarly provide enhanced echogenecity at certain locations of the stent to enhance visualization of selected features during ultrasound diagnostic procedures.

Using visualization techniques, if the placement of the stent is not optimal, the physician may readvance the constraining sheath to recapture the deployed segment of stent, reposition the delivery system, and attempt the deployment again. The ability to recapture the stent is another benefit of the closed cell architecture described above, and is another advantage to connecting all of the internal apices, particularly in the region of the stent that is first expanded. After the stent has been confirmed to be anchored in the intended location, the sheath is fully retracted, releasing the stent from the delivery system into position within the target vessel.

Once the stent has unloaded from its constrained diameter, it will contact the vessel. The chronic outward force of the stent will cause the vessel diameter, particularly at the point of the lesion, to enlarge to restore flow through the vessel. As a final step, it can be advantageous to inflate a balloon within the stent, particularly in the region of the subject obstructive lesions. The balloon can assist in expanding the stent, even past its normal expanded diameter. When the balloon is deflated, the stent is again subjected to loading stresses, and therefore resists recoil of the vessel according to the radial resistive force (RRF) driven by the higher stress response of the upper plateau. With this method, the outward forces localized in the area of the obstructive lesion are maximized to ensure maximum luminal gain and relief from the symptoms associated with IVCS.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. In addition, the intended uses of the present invention include a variety of medical applications as well as other applications where highly precise, compact devices for fluid transport are needed. It should be understood that various alternatives to these embodiments of the invention described herein may be employed in practicing the invention. It is intended at the following claims defined the scope of the invention and it methods and structures within the scope of these claims and their equivalents be covered thereby.

What is claimed is:

1. A method of inserting a stent, comprising:
    inserting a stent into a vessel, the stent comprising a first section and a second section, wherein the first section is more flexible along a longitudinal axis of the stent than the second section, the first section and the second section each including:
    a plurality of expandable modules, each expandable module including a plurality of strut elements that join together at a plurality of apices; and
    a plurality of bridging modules, each bridging module including bridging elements having a constant pitch that connect only an apex of a first module with only an apex of a second module such that every apex in an expandable module is connected to an apex in an immediately adjacent expandable module by a bridging element, wherein the plurality of bridging modules are arranged to alternate along the longitudinal axis between clockwise bridging modules and counterclockwise bridging modules, the clockwise bridging modules including bridging elements that extend at a fixed clockwise angle with respect to the longitudinal axis, and the counterclockwise bridging modules including bridging elements that extend at a fixed counterclockwise angle with respect to the longitudinal axis, wherein there are a greater number of bridging elements in the plurality of bridging modules around a circumference of the first section than the number of bridging elements in the plurality of bridging modules around a circumference of the second section wherein the second section is more radially stiff than the first section, the method further comprising aligning the second section with a specific region of the vessel that requires radial stiffness to counteract crushing force caused by surrounding anatomy; and
    aligning the first section with a specific region of the vessel that requires axial flexibility to accommodate surrounding anatomy.

2. The method of claim 1, wherein the vessel is a left iliac vein, and wherein the specific region is proximate to where a common femoral vein crosses underneath an inguinal ligament.

3. The method of claim 1, wherein the vessel is a vein, and wherein the specific region of the vessel that requires axial flexibility to accommodate surrounding anatomy is proximate to where a common femoral vein crosses underneath an inguinal ligament and the second section is more radially stiff than the first section and adapted and configured to provide a radial stiffness to counteract a crushing force caused by a inguinal ligament with the vein wall.

4. The method of claim 1 the stent further comprising a third section having expandable modules and bridging modules as in the first section, the third section positioned such that the second section is between the first section and the third section.

5. A method of inserting a stent, comprising:
    inserting a stent into a vessel, the stent comprising a first section and a second section, wherein the first section is more flexible along a longitudinal axis of the stent than the second section, the first section and the second section each including:
    a plurality of expandable modules, each expandable module including a plurality of strut elements that join together at a plurality of apices;
    a plurality of bridging modules, each bridging module including bridging elements that extend only from an apex of a first expandable module to only an apex of an immediately adjacent second expandable module wherein the first expandable module is connected with the second expandable module only by said bridging elements, wherein the first section of the stent has a greater number of bridging elements around a circumference of the first section than the number of bridging elements around a circumference of the second section;
    wherein the plurality of bridging modules are arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis, wherein the clockwise bridging modules including bridging elements that extend at a fixed clockwise angle with respect to the longitudinal axis, and the counterclockwise bridging modules including bridging elements that extend at a fixed counterclockwise angle with respect to the longitudinal axis;
    aligning the first section with a first specific region of the vessel that requires axial flexibility to accommodate surrounding anatomy; and
    aligning the second section with a second specific region of the vessel to provide radial stiffness to counteract a crushing force imparted by a surrounding anatomy.

6. The method of claim 5, wherein the vessel is a left iliac vein, and wherein the first specific region is proximate to where a left common iliac vein crosses an inguinal ligament.

7. The method of claim 5, wherein the vessel is a vein, and wherein the specific region of the vessel that requires axial flexibility to accommodate surrounding anatomy is proximate to where a left common iliac vein crosses an inguinal ligament and the second section is more radially stiff than the first section and adapted and configured to provide a radial stiffness to counteract a crushing force caused by a inguinal ligament with the vein wall.

8. The method of claim 5 wherein the length of the first section and the second section is selected to be sufficient to position the stent along a portion of the patient's venous vasculature to treat a cause of a venous thrombo-occlusive disease.

9. The method of claim 8 wherein the venous thrombo-occlusive disease is an occurrence of iliac compression disorder.

10. The method of claim 5 wherein the difference in the fixed clockwise angle and the fixed counterclockwise angle partially removes a bias to torsional loading in the stent during use.

* * * * *